(12) United States Patent
Ashitaka et al.

(10) Patent No.: US 10,577,393 B2
(45) Date of Patent: Mar. 3, 2020

(54) POROUS HOLLOW FIBER MEMBRANE

(71) Applicant: TOYOBO CO., LTD., Osaka-shi, Osaka (JP)

(72) Inventors: Satoru Ashitaka, Otsu (JP); Toru Uenishi, Otsu (JP); Noriko Monden, Otsu (JP); Noriaki Kato, Otsu (JP)

(73) Assignee: TOYOBO CO., LTD., Osaka-shi (JP)

( * ) Notice: Subject to any disclaimer, the term of this patent is extended or adjusted under 35 U.S.C. 154(b) by 0 days.

(21) Appl. No.: 14/428,858

(22) PCT Filed: Oct. 23, 2013

(86) PCT No.: PCT/JP2013/078702
§ 371 (c)(1),
(2) Date: Mar. 17, 2015

(87) PCT Pub. No.: WO2014/077095
PCT Pub. Date: May 22, 2014

(65) Prior Publication Data
US 2015/0232506 A1 Aug. 20, 2015

(30) Foreign Application Priority Data

Nov. 15, 2012 (JP) .................................. 2012-250826

(51) Int. Cl.
| | | |
|---|---|---|
| C07K 1/34 | (2006.01) |
| B01D 67/00 | (2006.01) |
| B01D 69/02 | (2006.01) |
| B01D 69/08 | (2006.01) |
| B01D 69/12 | (2006.01) |
| B01D 71/10 | (2006.01) |
| B01D 71/68 | (2006.01) |
| A61M 1/16 | (2006.01) |

(52) U.S. Cl.
CPC ............ *C07K 1/34* (2013.01); *B01D 67/0002* (2013.01); *B01D 67/003* (2013.01); *B01D 67/0088* (2013.01); *B01D 69/02* (2013.01); *B01D 69/08* (2013.01); *B01D 69/12* (2013.01); *B01D 71/10* (2013.01); *B01D 71/68* (2013.01); *A61M 1/1623* (2014.02); *B01D 2323/02* (2013.01); *B01D 2325/022* (2013.01)

(58) Field of Classification Search
CPC ...................................................... B01D 71/68
See application file for complete search history.

(56) References Cited

U.S. PATENT DOCUMENTS

| | | | |
|---|---|---|---|
| 4,794,002 A | 12/1988 | Henis et al. | |
| 4,826,599 A * | 5/1989 | Bikson | B01D 69/12 210/321.8 |
| 5,340,480 A * | 8/1994 | Kawata | B01D 67/0011 210/500.23 |
| 8,613,361 B2 * | 12/2013 | Ueno | B01D 63/02 210/490 |
| 2003/0015466 A1 * | 1/2003 | Ji | B01D 67/0011 210/500.25 |
| 2007/0084788 A1 | 4/2007 | Moya et al. | |
| 2009/0050555 A1 | 2/2009 | Baba et al. | |
| 2009/0110900 A1 * | 4/2009 | Yokota | B01D 69/02 428/221 |
| 2010/0133172 A1 * | 6/2010 | Song | B01D 67/0088 210/500.37 |
| 2010/0159143 A1 * | 6/2010 | Moya | A61L 2/0017 427/384 |
| 2011/0017654 A1 * | 1/2011 | Ueno | B01D 63/02 210/321.6 |
| 2012/0305472 A1 | 12/2012 | Yokota et al. | |

FOREIGN PATENT DOCUMENTS

| | | |
|---|---|---|
| JP | 64-038103 A | 2/1989 |
| JP | 06-165926 A | 6/1994 |
| JP | 07-014469 B2 | 2/1995 |

(Continued)

OTHER PUBLICATIONS

Notification of Transmittal of Translation of the International Preliminary Report on Patentability (Form PCT/IB/338) of International Application No. PCT/JP2013/078702 dated May 21, 2015 with Form PCT/IPEA/409 (5 pages).

International Search Report dated Nov. 19, 2013, issued in corresponding application No. PCT/JP2013/078702.

Extended (Supplementary) European Search Report dated May 13, 2016, issued in counterpart European Patent Application No. 13854249.3. (8 pages).

*Primary Examiner* — Ryan B Huang
(74) *Attorney, Agent, or Firm* — Westerman, Hattori, Daniels & Adrian, LLP

(57) ABSTRACT

A porous hollow fiber membrane is provided for the treatment of a protein-containing liquid, which can effectively separate and remove a substance such as a small diameter virus, and which can allow effective permeation of a useful substance to be recovered such as protein in high concentration. The porous hollow fiber membrane has an asymmetric structure having a dense layer in an outer layer only and contains a hydrophobic polymer and a first hydrophilic polymer, the surface and the porous part of the hollow fiber membrane are coated with a second hydrophilic polymer, the hydrophobic polymer is a polysulfone-type polymer, the first hydrophilic polymer is a copolymer of vinylpyrrolidone with vinyl acetate, and the second hydrophilic polymer is a polysaccharide or a polysaccharide derivative. The porous hollow fiber membrane is obtained by co-dissolving the hydrophobic polymer and the first hydrophilic polymer and then the second hydrophilic polymer is coated.

7 Claims, No Drawings

(56) References Cited

FOREIGN PATENT DOCUMENTS

| JP | 2005074019 A | * | 3/2005 |
|----|---|---|---|
| JP | 2007-136449 A | | 6/2007 |
| JP | 2011-072987 A | | 4/2011 |
| WO | 2006/080482 A1 | | 8/2006 |
| WO | 2009/123088 A1 | | 10/2009 |
| WO | 2011/111679 A1 | | 9/2011 |

* cited by examiner

POROUS HOLLOW FIBER MEMBRANE

TECHNICAL FIELD OF THE INVENTION

The present invention relates to a porous hollow fiber membrane for the treatment of a protein-containing liquid by which recovery of a permeating substance such as protein and trapping of fine particles such as virus can be efficiently carried out in the case of separation and purification of a protein-containing liquid, etc. More particularly, it relates to a porous hollow fiber membrane consisting of a polysulfone-type polymer and two kinds of hydrophilic polymers which are a copolymer of vinylpyrrolidone with vinyl acetate and a cellulose-type polymer and having a dense layer in its outer layer.

BACKGROUND ART

A hollow fiber membrane for a purpose of liquid treatment has been widely utilized in industrial uses such as microfiltration and ultrafiltration and in medical uses such as hemodialysis and plasma separation. Particularly in recent years, there has been a demand in the field of pharmaceutical industry for an art of elimination of not only bacteria but also pathogenic substances in nano sizes such as virus during production steps so as to ensure high safety for bio-pharmaceutical drugs and blood products. The drug and the blood product as such are produced from a substance derived from living organisms such as protein by means of the steps such as incubation, recovery and purification. Accordingly, there is a risk of contamination of small amount of components derived from such materials and auxiliary materials (such as culture medium and water). Among them, virus contaminating therein is a highly risky component even if its amount is very small.

With regard to a method for removing and inactivating the virus, there are removal methods by means of a heating treatment, a highly energetic treatment with irradiation of gamma ray, ultraviolet ray, etc., a chemical treatment such as a treatment at low pH and a treatment using surfactant, a precipitation/fractionation method such as an ethanolic fractionation and an ammonium sulfate fractionation, chromatography and membrane filtration. Ability of a step for excluding the virus from the step is called a virus clearance. Among them, according to the membrane filtration method, affection to denaturation of protein to be recovered is small and even such a virus which is energetically and chemically resistant can be removed. Therefore, the membrane filtration method has been thought to be a useful method because it enables a sure separation/removal mainly due to a sieving effect. The membrane filtration method is a very reliable and highly efficient method in a process for removing virus from a solution of protein having smaller size than the virus so as to recover the protein. It is a matter of course that sharpness of separation size and completeness having no deficiency are demanded for a separation membrane used for removing the virus.

Moreover, in a process for producing bio-pharmaceutical drugs and blood products, protein which is a useful ingredient should be efficiently recovered in terms of productivity and yield. However, in such a case wherein the membrane has a pore size which guarantees sure removal of virus, sure removal of virus is guaranteed whereas property of protein recovery by permeation or life of the membrane lowers due to clogging of the membrane as the size of the protein to be recovered becomes near the size of virus. It is usual that, in such a use, pore size of the membrane is designed by placing a focus on the virus of the smallest size which is worried about as the contaminant virus (parvovirus having diameter of about 20 nm has been presumed to be a representative one). In that case, protein in an immunoglobulin region is a protein ingredient having the processible size in almost upper limit. Since the separation of protein and virus is conducted depending upon the sizes thereof as such, recovery of protein having bigger size than, for example, parvovirus is impossible by a membrane which guarantees removal of parvovirus. In such a case, only the virus clearance to virus in a size depending upon the membrane size (such as retrovirus) is guaranteed by a virus filtration membrane while, with regard to virus in small sizes permeating the membrane, the virus clearance of the step is guaranteed by a production process warranted by other removal or inactivating step. They are appropriately selected by producers depending upon the target protein of bio-pharmaceutical preparations and blood products to be recovered.

As mentioned above, when that which is predicted as the smallest virus in general is taken as a removal target, high removal of substances in a parvovirus size and good recovery of substances in a globulin size can be important indicators for the safety and the performance. In the process for producing drugs, it goes without saying that security of safety as quality of the preparations has the first priority. Therefore, it cannot be denied that the productivity such as permeation and recovery of protein becomes a victim to some extent. There has been a demand for the development of virus removing membrane which satisfies both of them. Since the productivity mentioned herein is also related to the cost of the preparations, there is a need for a production technique in a purifying step for providing the product at lower cost. Accordingly, it is the necessary technique in which the permeation characteristic of protein is enhanced while the pore size by which inhibition of virus can be surely inhibited is still retained.

Since a step for removing virus in bio-pharmaceutical drugs and blood products is carried out after a purifying step for achieving sufficient purity, there is such a characteristic that the factor affecting the permeability of the membrane to a solute is not the clogging and the blocking by a substance such as virus having bigger size than membrane pore size but the clogging due to the solute substance per se. Only a protein solution having such a property achieves the practical efficiency for the removal of virus by means of membrane separation. Accordingly, a step for filtrating almost pure protein solution can be said to be an actual virus removing step in a membrane method. In view of such a sense, it is likely that a decrease in permeability of a solute protein is caused by the clogging due to adsorption of protein per se (which can be said to have sufficiently high permeability in view of its size) with the pores and also by the blocking of pores.

It is supposed that adsorption of protein is mostly due to an interaction of the hydrophobic domain in protein and the hydrophobic surface of a membrane material. There is usually carried out a method wherein a hydrophilized membrane is used for a purpose of reducing the adsorption. This is a means which is widely used in membranes for blood purification, membranes for water purification, etc. as well. There have been conducted, for example, a method wherein membrane is manufactured from a hydrophilic polymer, a method wherein a hydrophobic polymer is a main constituent of a membrane and a hydrophilic polymer is blended in the materials to form a membrane, a method wherein, after a hydrophobic polymer membrane is manufactured, it is coated with a hydrophilic polymer.

Further, in order to achieve the higher productivity, it is also effective that not only the stability of filtration but also the permeation speed of the solution to be treated are made high. This is possible by making the water permeation coefficient of the membrane itself large and by making the operation pressure for the filtration high. Thus, the permeated liquid amount per unit time and unit area is determined by a product of the water permeation coefficient and the operation pressure. A designing matter for increasing the water permeation speed from the membrane structure is expansion of the pore size and reduction of the membrane thickness but, there is a limitation for warranting the exclusion of virus and for making the pore size large whereby that is not preferred. Accordingly, it is an effective membrane design that the membrane thickness is made as small as possible so that the resistance to water permeation is reduced. When the operation pressure is higher, the amount of permeated water can be increased but, since it also depends upon the durability of membrane and also upon the strength of piping of the apparatus as a whole, it is preferred to be made high within an extent allowable therefor. In a manufacturing step, it is usual that not only metal pipe but also silicon tube is used for the piping. Accordingly, an operation pressure is set in such a manner that its upper limit is about 3 to 4 bars. Desirable membrane is such a one which can be used as near as possible the upper limit within the above range. Needless to say, it is not preferred in view of guaranteeing the high virus-removing ability that application of pressure causes deformation of the membrane, changes and variations in the pore, etc. Accordingly, stability of the strong pore is also the necessary condition. Further, in such a case wherein a protein solution is filtrated at high pressure, there is a problem that, when adsorption to the membrane takes place, the adsorption becomes stronger due to the consolidation of a solute component whereby, for example, multi-layered adsorption is apt to be induced.

In addition, a very effective means for making the production of bio-pharmaceutical preparations and blood products efficient is to operate the liquid to be treated in a concentration of as high as possible. Although the concentration of the final preparation as a drug is decided in each of the products, in the intermediate processes for incubation and purification, treatment is not conducted as the liquid of this final concentration. When the treatment and the handling are conducted in a concentration of as high as possible, scale of the apparatus becomes compact and big advantages are resulted for the efficiency such as the time for feeding the liquid and the time for conducting the filtration operation. Accordingly, even in a filtration membrane, there is also a demand for the ability for treating a protein solution in a concentration of as high as possible within short time.

Patent Document 1 discloses a virus-retaining ultrafiltration membrane having a surface which is made hydrophilic using hydroxyalkyl cellulose. According to Patent Document 1, a surface of a hydrophobic polymer membrane is made hydrophilic using hydroxyalkyl cellulose, and the surface is treated in an autoclave or is immersed in boiling water whereby performance as a membrane for virus removal can be enhanced. The reason therefor is mentioned that hydrophilicity (angle of contact) increases by the treatment at 100° C. or higher and also that a hardly swelling state is resulted whereby improvement to a preferred mode is achieved. The resulting effect as such is likely to be an effect which is specific to the constitution of a membrane wherein a hydrophobic polymer is coated with hydroxyalkyl cellulose. It is not possible to further expand the effect to such a membrane wherein a membrane before the coating is hydrophilic (i.e. a membrane solely comprising a hydrophilic polymer or a blended membrane with a hydrophilic polymer). It is likely that, in the membrane as such, the membrane itself before the coating hardly retains the stability which can guarantee the inhibition of virus under the condition such as autoclaving or the membrane itself before the coating exhibits a swelling ability whereby it is presumed that the effect disclosed in this document cannot be achieved. In Patent Document 1, a filtrating operation at 30 psi (about 2 bar) is carried out and, as compared with a membrane wherein only a hydrophilic polymer is blended, it is likely that the stability of the operation at high pressure is also enhanced.

In a membrane wherein the hydrophilization of the membrane is done by a single hydrophilic polymer, it sometimes happens that a membrane surface wherein the hydrophilic polymer component is fully exposed is not always formed or all of the membrane surfaces or all of inner pore areas are not always coated when a hydrophobic polymer is blended with a hydrophilic polymer or is coated therewith. With regard to the causes therefor, it has been clarified according to the recent surface analysis technique that each of the hydrophobic and hydrophilic polymers is solely apt to have a domain structure and that, when the membrane surface is observed in a microscopic manner, those polymers (a hydrophilic polymer in many cases) are present in a separated state in a patch form. In that case, it is possible to further improve and optimize the hydrophilizing function by means of compounding a plurality of polymers. Moreover, the use of a hydrophilic polymer has a problem that elution of the hydrophilic polymer is resulted and there is a possibility that contamination of this component is generated in the treatment solution. Particularly in the case of use for medical purpose and for drug production, there is also predicted a sterilizing treatment by heat or by drug or a washing treatment and, in addition, a reuse or the like whereby its adaptability is important.

Further, when the membrane is coated with another hydrophilic polymer after formation of the membrane, it goes without saying that the possibility of the affection such as narrowing, clogging, etc. of the pores by the hydrophilic polymer used for the coating is to be taken into consideration. In that case, the relation between the molecular size of the polymer used for the coating and the pore size is particularly important and careful attention is necessary therefor. When a hydrophilic polymer having a sufficiently small molecular size to the pore size is used for the coating, risk of the clogging is relatively small but, when the molecular weight is small, no sufficient retention of adsorption ability is achieved and dropout is apt to happen.

In Patent Document 2, there is disclosed an art wherein a porous membrane consisting of a hydrophobic polymer is coated with a second hydrophilic polymer having higher hydrophilicity via a coating layer of a copolymer of polyvinyl alcohol with vinyl acetate. According to Patent Document 2, since the coating layer of the copolymer of polyvinyl alcohol with vinyl acetate is insoluble in water, it can form a stable coating layer for a hydrophobic polymer. On the other hand, since the copolymer of polyvinyl alcohol with vinyl acetate exhibits small hydrophilicity whereby it has no high suppressive ability for adsorption of protein or the like, the second highly hydrophilic polymer is further applied in order to improve such a point so as to achieve the hydrophilicity. A hydrophobic unit (vinyl acetate moiety) of the copolymer of polyvinyl alcohol with vinyl acetate contributes in enhancing the adsorption stability of the hydrophobic polymer of the substrate material while a hydrophilic unit (vinyl alcohol moiety) contributes in enhancing the adsorption stability of the second hydrophilic polymer. When the copolymer of polyvinyl alcohol with vinyl acetate is prepared by blending with a hydrophobic polymer, compatibility with the hydrophobic polymer is necessary but a high hydrogen-bonding ability of polyvinyl alcohol becomes a hindrance whereby it results in a phase separation from the hydrophobic polymer as well upon the stage of phase separation (resulting in a micro-domain structure) and, in addition, a solution composition in the preparation of a spinning dope is also very limited. Due to those reasons, it is presumed that those methods are substantially limited for the adaptation to a coating method as mentioned in Patent Document 2. In addition, when the second hydrophilic polymer is fixed to the first hydrophilic polymer (a copolymer of polyvinyl alcohol with vinyl acetate in Patent Document 2) by means of adsorption, it is desirable that the first hydrophilic polymer is not re-dissolved in a coating liquid in which the second hydrophilic polymer is dissolved. In Patent Document 2, there is disclosed such an idea, for example, to use a coating liquid in which saponification degree of the copolymer of polyvinyl alcohol with vinyl acetate is adjusted to low saponification degree exhibiting no water solubility. In addition, formation of a composite polymer thin membrane layer by means of a stepwise coating has such problems of the troublesomeness in membrane preparation by the treatment of coating solutions for a plurality of times and the affection to the substrate membrane itself by the influence of an organic solvent used for coating the copolymer of polyvinyl alcohol with vinyl acetate. Moreover, when an anchor effect to a hydrophobic polymer by the copolymer of polyvinyl alcohol with vinyl acetate is not fully achieved, there is also such a possibility that elution of a coating component becomes much and that hydrophilization becomes insufficient as well. When the hydrophobic solute (such as protein) contacts such a membrane, there is resulted a competitive adsorption with a coating polymer (in this case, it is a copolymer of polyvinyl alcohol with vinyl acetate) against a hydrophobic moiety of the substrate polymer and, if the adsorption with a solute component has a priority in terms of energy, exchange of the adsorbing component happens, which leads to the dropout of the coated polymer. In view of such a point, the polymer having a binder function contributing in a binding of a hydrophobic polymer with a highly hydrophilic polymer cannot be said to be sufficient only by means of the coating to a hydrophobic polymer. As such, Patent Document 2 uses the specificity by partial saponification of the copolymer of polyvinyl alcohol with vinyl acetate and it gives neither expansion to other materials and combinations nor suggestion therefor.

In Patent Document 3, there is shown a separation membrane consisting of (A) a hydrophobic polymer, (B) a polymer consisting of a hydrophilic unit only and (C) a copolymerized polymer consisting of a hydrophilic unit and a hydrophobic unit. To be more specific, (A) is a polysulfone type polymer, (B) is polyvinylpyrrolidone or polyethylene glycol and a hydrophilic unit in (C) is vinylpyrrolidone or ethylene glycol while a hydrophobic unit in (C) is vinyl acetate or vinylcaprolactam, and a membrane consisting of a blend of the component (A) and the component (B) is coated with the polymer of the component (C). In the constitution consisting of those three components, a membrane consisting of a hydrophobic polymer and a hydrophilic polymer (the component (A) and the component (B)) is further coated with the third component (the component (C)). When a copolymerized polymer partly having a hydrophobic unit is used instead of just a hydrophilic polymer as the third component, the hydrophobic unit exhibits an adsorbing ability to a hydrophobic moiety being exposed on the surface of a membrane consisting of a blend of two components which are a hydrophobic polymer and a hydrophilic polymer. As a result thereof, it is an object that the exposed hydrophobic moiety is mitigated by the component (C). Accordingly, it is ideal that surfaces of the membrane pores are formed only from the two components which are the hydrophobic polymer (the component (B)) and the copolymerized polymer (the component (C)). However, it can be easily presumed that the surface characteristic as such will result in a problem of extent that, when the affection by the exposed area of the component (A) is compared with the affection by the hydrophobic unit of the component (C), then which will be in less bad affection in terms of hydrophobicity. Thus, it is obvious that the membrane of the Patent Document 3 is inferior in terms of hydrophilicity to a membrane coated with the polymer which is entirely consisting of a hydrophilic unit (such as that in Patent Document 4). If and when a polymer solely consisting of a hydrophilic unit (such as cellulose type polymer, polyvinylpyrrolidone or polyethylene glycol which is exemplified in Patent Document 4) is used as the component (C) in Patent Document 3, the fixing force of the coat is weak and that is not preferred whereby there is a limitation in a combination of the component (B) with the component (C). Accordingly, in the art as shown in Patent Document 3, although the priority in a micron size such as adsorption of platelets mentioned in its text is noted, a high permeability of protein which is an object of the present invention cannot be expected. In addition, as mentioned already, the membrane before the coating (consisting of the component (A) and the component (B)) itself has a swelling property whereby it is predicted that the high stability of pore size and the resistance to pressure are not sufficient.

PRIOR ART DOCUMENTS

Patent Documents

Patent Document 1: Japanese Patent Application Laid-Open (JP-A) No. 2007-136449

Patent Document 2: Japanese Patent Application Laid-Open (JP-A) No. 38103/89

Patent Document 3: Japanese Patent Application Laid-Open (JP-A) No. 2011-72987

Patent Document 4: Japanese Patent Pregrant Publication (JP-B) No. 14469/95

DISCLOSURE OF THE INVENTION

Problem that the Invention is to Solve

The present invention has been achieved in view of the current status of the conventional art as mentioned above and its object is to provide a porous hollow fiber membrane for the treatment of a protein-containing liquid which enables efficient permeation of a useful substance such as protein and, at the same time, high suppression of a substance to be removed such as virus.

Means for Solving the Problem

The present inventors have conducted extensive investigations for achieving the above-mentioned object and found that, when a membrane structure having a dense layer in the outer layer only is adopted and a first hydrophilic polymer forming a hollow fiber membrane together with a hydrophobic polymer and also a second hydrophilic polymer coating the hollow fiber membrane are selected in an optimum manner, it is now possible to trap fine particles such as virus and to efficiently permeate the protein being smaller than such fine particles. Based on these findings, they have accomplished the present invention.

Thus, the present invention has the constitution of the following (1) to (7).

(1) A porous hollow fiber membrane for the treatment of a protein-containing liquid, characterized in that the hollow fiber membrane consists of an asymmetric structure having a dense layer in an outer layer only and contains a hydrophobic polymer and a first hydrophilic polymer, that the surface and the porous part of said hollow fiber membrane are coated with a second hydrophilic polymer, that said hydrophobic polymer is a polysulfone-type polymer, that said first hydrophilic polymer is a copolymer of vinylpyrrolidone with vinyl acetate, and that said second hydrophilic polymer is a polysaccharide or a polysaccharide derivative.

(2) The porous hollow fiber membrane according to (1), wherein said second hydrophilic polymer is a cellulose type polymer.

(3) The porous hollow fiber membrane according to (1) or (2), wherein the amount of said first hydrophilic polymer contained in the membrane is 5 to 9% by weight.

(4) The porous hollow fiber membrane according to any of (1) to (3), wherein the amount of said second hydrophilic polymer contained in the membrane is 0.5 to 2.5% by weight.

(5) The porous hollow fiber membrane according to (4), wherein the ratio by weight (IR/NMR) of the amount (IR) of the first hydrophilic polymer existing near the outer surface by an IR measurement to the amount (NMR) of the first hydrophilic polymer existing in the whole membrane by an NMR measurement is 0.9 to 1.1.

(6) The porous hollow fiber membrane according to any of (1) to (5), wherein, when the absorbance of an extract is measured under the condition of 200 to 350 nm wavelength range and 1 cm cell length, the resulting maximum absorbance is 0.1 or less, wherein the extract has been prepared by such a manner that 1 g of a bundle of the hollow fiber membrane in a dry state is weighed, immersed in 100 g of water and subjected to an autoclave extraction for 20 minutes with the reaching/retaining temperature of 132° C.

(7) A method for manufacturing the porous hollow fiber membrane for the treatment of a protein-containing liquid mentioned in any of (1) to (6), characterized in that said method comprises a step wherein a porous hollow fiber membrane is formed using a dope prepared by co-dissolving the hydrophobic polymer and the first hydrophilic polymer in the same solvent and then the second hydrophilic polymer is coated on the surface and the porous part of the hollow fiber membrane.

Advantages of the Invention

The porous hollow fiber membrane of the present invention has a specific layer structure and is formed using a specific hydrophobic polymer and two kinds of hydrophilic polymers. Accordingly, it can be utilized for the separation of virus from a protein solution and can particularly remove virus in a high level and, at the same time, it can efficiently permeate the protein. Consequently, the porous hollow fiber membrane of the present invention can be advantageously used as a membrane for removing the impurities such as virus from a solution of protein which is a useful substance, in a method for manufacturing bio-pharmaceutical drugs and blood products.

BEST MODE FOR CARRYING OUT THE INVENTION

As hereunder, the porous hollow fiber membrane of the present invention will be illustrated in detail.

In the porous hollow fiber membrane of the present invention, a second hydrophilic polymer which is in a different type from a first hydrophilic polymer is adsorbed with and fixed on the surface of a hollow fiber substrate membrane containing a hydrophobic polymer and the first hydrophilic polymer. The hollow fiber substrate membrane consists of a blended polymer of the hydrophobic polymer with the first hydrophilic polymer which are compatible with each other and is manufactured from a solution of both polymers in a common solvent. As to the hydrophobic polymer, there is used a polysulfone-type polymer such as a polysulfone (hereinafter, it may be abbreviated as PSf) which is a polymer having a repeating unit represented by the following formulae [I] and [II] or a polyether sulfone (hereinafter, it may be abbreviated as PES). The polysulfone-type polymer is advantageous for preparing a membrane having high water permeability and is a material being excellent in processing into a uniform membrane, an asymmetric membrane, etc. The polysulfone-type polymer may contain a functional group or a substituent such as an alkyl group. Hydrogen atom in the hydrocarbon skeleton may be substituted with other atom such as halogen or with a substituent. In addition, this is preferred to be used solely and, with regard to its molecular weight, the use of a relatively high one is preferred.

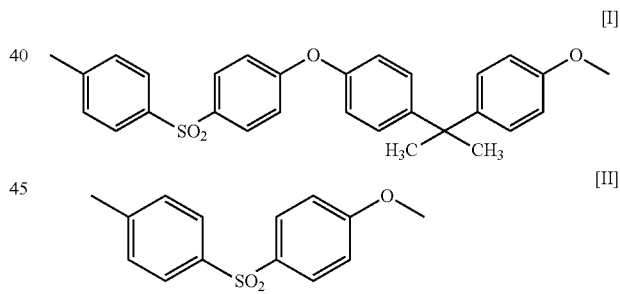

With regard to the first hydrophilic polymer, there is used a copolymer wherein vinylpyrrolidone and vinyl acetate are used as a hydrophobic unit and a hydrophilic unit, respectively (hereinafter, it may be abbreviated as VA copolymer). With regard to a VA copolymer, a copolymer wherein the ratio by weight of vinylpyrrolidone to vinyl acetate is 6:4 (hereinafter, it may be abbreviated as VA 6/4) and a VA 65/35 wherein the ratio by weight of vinylpyrrolidone to vinyl acetate is 65:35 are preferred because they are excellent in terms of, for example, imparting the hydrophilicity to a polysulfone-type membrane and also of being excellent in compatibility with a polysulfone-type polymer. Seen from a view of hydrophilicity and hydrophobicity, vinylpyrrolidone is a hydrophilic component and vinyl acetate is a hydrophobic component. A balance between hydrophilicity and hydrophobicity in those copolymers is dependent upon the copolymerized composition.

As to a hydrophilizing agent for a polysulfone-type membrane which has been utilized in the use for blood purification and for water treatment, it has been common to use polyvinylpyrrolidone (hereinafter, it may be abbreviated as PVP) which is a homopolymer of vinylpyrrolidone. The art as such has been utilized as a common art due to the following reasons that compatibility of both polymers is good, that controlling ability for pore formation by micro phase separation when an aqueous non-solvent is used and that appropriate hydrophilicity can be easily imparted to a membrane. However, in a membrane consisting of a blended polymer of a polysulfone-type polymer with PVP, diffusion and partition to an aqueous coagulating phase side are relatively high due to high hydrophilicity of PVP in a phase separation process. Accordingly, pore formation is dependent upon a phase separation accompanied by the transfer of not only lower molecules such as a solvent but also PVP (a polymer component) whereby there is a tendency that distribution of the pore size becomes broad. In accordance with the present invention, a VA copolymer having lower hydrophilicity than PVP is used to a polysulfone-type polymer whereby it is possible to achieve a high separation ability between virus and protein. Further, a VA copolymer can stably dissolve both components in higher concentrations than PVP in the preparation of its mixed solution (a spinning dope) with a polysulfone-type polymer whereby a spinning region for manufacturing a hollow fiber substrate membrane can be made broad and it contributes in designing the optimum condition. Particularly in such a case wherein the phase separation ability is controlled by addition of a non-solvent to a spinning dope as shown in the present invention, it is important that a stable mixed solution can be prepared. In addition, by using a blended polymer of a polysulfone-type polymer with a VA copolymer, it is also possible to suppress the changes in the membrane property caused by swelling due to water which is the above-mentioned problem, thanks to the presence of a hydrophobic component of the VA copolymer. As such, in the present invention, a VA copolymer plays a role of not only imparting the hydrophilicity to a polysulfone-type membrane but also controlling the membrane structure.

As to the second hydrophilic polymer, polysaccharide or a polysaccharide derivative is used. In the case of a cellulose-type polymer, hydroxylalkyl cellulose is preferred. Hydroxyethyl cellulose and hydroxypropyl cellulose (hereinafter, it may be abbreviated as HPC) may be exemplified. As to the polysaccharide other than a cellulose-type one, starch, dextran and curdlan may be exemplified. Weight-average molecular weight of the second hydrophilic polymer is preferred to be 140,000 or less for a purpose of avoiding an increase in the solution viscosity and in view of the permeation efficiency into the membrane. Depending upon the pore size of the aimed membrane, it is also preferred to appropriately lower the molecular weight. In the present invention, it is preferred that, after a hollow fiber substrate membrane containing the hydrophobic polymer and the first hydrophilic polymer is manufactured, the hollow fiber substrate membrane is immersed, for example, in a solution or a dispersion containing the second hydrophilic polymer so as to adhere the second hydrophilic polymer. In that case, it is preferred that, after an excessive first hydrophilic polymer is removed by washing from a polysulfone-type membrane containing the first hydrophilic polymer, the second hydrophilic polymer is adhered to membrane surface and pore surface. The present inventors have found that, when a polysulfone-type membrane containing a VA copolymer as the first hydrophilic polymer as mentioned above is coated with the second hydrophilic polymer consisting of a cellulose-type polymer, it is possible to retain stable and high hydrophilicity and to suppress elution of the VA copolymer.

Inner diameter of the porous hollow fiber membrane of the present invention is preferred to be 150 μm to 310 μm, more preferred to be 160 μm to 250 μm, and further preferred to be 180 μm to 230 μm. When the inner diameter is less than that, pressure loss of the liquid running through the hollow area of the hollow fiber membrane becomes high and the filtrating pressure may become non-uniform in the lengthwise direction of the hollow fiber membrane. Further, when a liquid to be treated which contains abundant impurities and coagulating components is introduced, there is a possibility that the inner area may be clogged due to the components in the liquid to be treated. When the inner diameter is more than that, collapse and distortion of the hollow fiber membrane are apt to happen. Furthermore, the membrane thickness is preferred to be 50 μm to 80 μm and more preferred to be 52 μm to 75 μm. When the membrane thickness is less than that, collapse and distortion of the hollow fiber membrane are apt to happen. When the membrane thickness is more than that, resistance when the liquid to be treated runs the membrane wall becomes high and permeability may become lower.

In view of the durability to the pressure which is applied when the filtration is conducted, it is preferred that, in the porous hollow fiber membrane of the present invention, inner surface side of the hollow fiber membrane is used as the upstream side of the filtration so as to conduct the filtration from inside to outside. Moreover, since the use for recovering the filtrate is presumed, the filtrating method is preferred to be a dead end filtration.

In the porous hollow fiber membrane of the present invention, its membrane surface of the upstream side is in a rough structure as compared with the membrane surface of the downstream side and it consists of an asymmetric structure having a dense layer in the outer layer of the hollow fiber membrane. Such a structure plays a role of making the flow of the filtrate appropriately disturbed and achieves such an effect that the component affecting the clogging such as a coagulated product is hardly adsorbed with the membrane surface. As a result, it is now possible to reduce the lowering of filtration speed due to clogging of the inner surfaces of the membrane and even a protein solution of a relatively high concentration can be treated within short time.

It is preferred that the porous hollow fiber membrane of the present invention is in such an asymmetric structure that the densest area (a dense layer) exists on the outer side in the cross-sectional direction of the membrane. Structure of the membrane can be easily confirmed by observing, for example, under an electron microscope. Since an object of the porous hollow fiber membrane of the present invention is to highly remove a very small substance such as virus, the very small substance should be surely trapped in any of the parts of the thick area of the membrane. The substance to be trapped such as virus is trapped during the course of passing through the pore paths existing in the thick area of the membrane (which is called a depth-type filtration) and, due to the existence of the smallest pore area of the dense layer in the outlet, nearly 100% of removal can be guaranteed. When a dense layer exists in an inlet area, it is also possible to trap there (which is called a screen filtration). However, in that case, the trapping is locally done in the inlet area and, as a result, permeation degree of a solute to be passed through lowers due to narrowing of pore size and due to accumulation, or lowering of the amount of the permeated liquid is induced due to the clogging as the filtration proceeds whereby that is not preferred.

In the porous hollow fiber membrane of the present invention, amount of the first hydrophilic polymer contained in the membrane is preferred to be 5 to 9% by weight. It is more preferred to be 6 to 8% by weight. When the amount of the first hydrophilic polymer contained in the membrane is more than the above upper limit, its swelling in the membrane becomes big causing the instabilization of pore size and the lowering of resistance to pressure whereby the affection thereby on the suppression of virus and on the permeability of protein may not become negligible. Moreover, when the amount of the first hydrophilic polymer contained in the membrane is too much, there may happen such an inconvenience that, during the use, the first hydrophilic polymer is eluted and mixed into a recovered liquid. When the amount thereof is less than the above-mentioned lower limit, an ability of removing the virus may lower presumably because of the insufficient contribution to the membrane structure control. The amount of the first hydrophilic polymer as such can be measured by means of nuclear magnetic resonance (hereinafter, it may be abbreviated as NMR). In addition, the amount contained within a limited area near the surface of the membrane can be measured by means of surface infrared analysis (hereinafter, it may be abbreviated as IR). The term reading "near the surface" used hereinabove is a depth range wherefrom the molecular oscillation information by a surface IR analysis method can be obtained and the depth can be decided by the angle of incidence of IR ray, the refractive index of a specimen and the measured wave number. In the analysis of a polysulfone material near 1600 cm$^{-1}$ when angle of incidence is 45°, the area near the surface is usually a few μm (1 μm to 2 μm) from the surface. In such a case wherein the membrane thickness is 50 μm to 80 μm as shown in the present invention, the area near the surface is an area corresponding to the surface layer area to an extent of several % of the membrane thickness. The amount of the first hydrophilic polymer near the surface in the measurement by IR is not always the same as the amount in the whole membrane by NMR. That is presumed to reflect the bias of the distribution of the first hydrophilic polymer in the membrane. As a result, when the difference between the measured data by IR and the measured data by NMR is evaluated, it can be an indicator for judging the homogeneity of the distribution of the first hydrophilic polymer in the membrane. In a blended polymer membrane of an asymmetric type prepared by dissolution of a hydrophobic polymer and a hydrophilic polymer in a common solvent, the bias in the distribution as such is often observed. This is because, the phase separation and dropout behavior of the hydrophilic polymer in inner and outer sides of the hollow fiber membrane are different. Such difference will lead to variation of the blended polymer composition contained therein between the surface and the inner area. In the present invention, it is preferred that the difference in distribution of the hydrophobic polymer and hydrophilic polymer between the whole area and on the outer surface having a dense layer is small. If the difference is big, anisotropy in swelling and hydrophilicity is resulted in the membrane thickness direction whereby local generation of adsorption of protein is resulted disturbing the stable filtration. The ratio of IR/NMR is preferably 0.90 to 1.10 and more preferably 0.93 to 1.05.

In the porous hollow fiber membrane of the present invention, the amount of the second hydrophilic polymer contained in the membrane is preferred to be 0.5 to 2.5% by weight, and more preferred to be 0.7 to 2.2% by weight. When the amount of the cellulose-type polymer contained in the membrane is more than the above-mentioned upper limit, the effect of imparting the hydrophilicity to the membrane is saturated resulting in an excessively imparted amount. As a result, pores are clogged due to swelling in the pores whereby water permeability and protein permeability may lower. When the amount is less than the above-mentioned lower limit, adsorption of the hydrophilicity-imparting protein is generated whereby a treating amount for a protein solution may significantly lower. Coating of the second hydrophilic polymer also has an effect of suppressing the elution of the first hydrophilic polymer. Hereinabove, the amount of the cellulose-type polymer which is the second hydrophilic polymer is measured by NMR as the amount in the whole membrane. With regard to the second hydrophilic polymer, the value represented by the whole amount is taken as a preferred range because the second hydrophilic polymer is coated to whole membrane.

In the porous hollow fiber membrane of the present invention, its breaking strength is preferred to be 40 g/filament to 100 g/filament so as to withstand dynamic stress to the hollow fiber membrane such as the damage of a membrane resulted during its transportation and a step of making into a module, the pressure shock generated upon a work of installing a module to an apparatus and a filtration operation, etc. The breaking strength is more preferred to be 45 g/filament to 90 g/filament and further preferred to be 50 g/filament to 80 g/filament. Since it is an object of the porous hollow fiber membrane of the present invention to completely inhibit (more than 99.99%) the very small substance such as virus, it is necessary to prevent breakage and even small damage of the hollow fiber membrane. For such a purpose, it is better when the breaking strength is higher. On the other hand, for increasing the strength, a rise in the membrane thickness and a rise in the membrane density are needed whereby it is not necessary to increase the strength too much. Therefore, the above-mentioned preferred upper limit value is naturally present.

In the porous hollow fiber membrane of the present invention, it is preferred that, when the membrane is immersed in a water tank and compressed with gas from the hollow part of the membrane, a burst strength (burst pressure) is 7.5 bar or more. When a dead-end filtration under the pressurized state is presumed in case a liquid to be treated is flown into the hollow part of the porous hollow fiber membrane, the pressure resistance to the inner pressure is preferred to be higher. For example, when a constant rate filtration is carried out, a quick rise of the filtration pressure within short time may happen in the latter stage of the filtration. Accordingly, it is preferred that the pressure resistance is at least higher than 8 bar. The pressure resistance is more preferred to be higher than 9 bar. Moreover, in the pressure of the burst pressure or lower, it is not preferred that expansion of the pore due to the swelling by pressure takes place. Under the pressure of about 1 to 3 bar which is the common operating pressure, it is necessary that there is almost no expansion of the pore. If it is an operation pressure of one half or less of the burst pressure, there will be no problem. However, swelling property of a membrane is also related to the stabilization of this behavior and, for achieving the sure stability, it is necessary as mentioned above that the first hydrophilic polymer also contains a hydrophobic unit.

In the porous hollow fiber membrane of the present invention, permeation rate of pure water (hereinafter, it may be abbreviated as pure water flux) at 25° C. is preferred to be 50 to 500 L/(m$^2$·h·bar). Pure water flux can be an indicator for the filtration characteristic of porous membrane and can be a reference in the design matter for the user such as that how much membrane area and how much pressure is to be used for the operation in achieving the predetermined permeated liquid when a membrane of a predetermined flux value is used. Particularly when recovery of a permeable solute is an object, it is also possible to cope with the design by means of rough estimation or the like taking the viscosity of the liquid into consideration. In the present invention, the above flux is set at the optimum value for a region wherein the removal of virus and the permeation of protein are the subjects. When the pure water flux is lower than the above value, an efficient treatment becomes difficult due to such problems that the time for filtration becomes long and that many membrane areas become necessary. When the pure water flux is more than the above value, pore size becomes excessively big and it becomes difficult to highly separate/remove the substance to be removed such as virus. The pure water flux is more preferred to be 80 to 400 L/(m$^2$·h·bar) and further preferred to be 100 to 350 L/(m$^2$·h·bar).

In the filtration method when the porous hollow fiber membrane of the present invention is used, there are two types—constant pressure filtration and constant rate filtration. Constant pressure filtration is such a method wherein a predetermined filtration pressure is applied to a filtration membrane for permeating the filtrate. In the constant pressure filtration, together with the clogging of the membrane, the filtration rate lowers. Constant rate filtration is such a method wherein filtration is conducted at constant flow rate. In the constant rate filtration, together with the clogging of the membrane, the filtration pressure arises. Each of those methods is appropriately selected depending upon the specification of the apparatus of the user and upon the characteristic of the manufacturing process. It is preferred that the membrane is capable of adapting to any of the methods. In the constant pressure filtration, the fact whether a filtration is suitably conducted or not is judged based on the product of the amount of the filtrate and the permeability of the solute within a predetermined time. The ratio (recovery rate) of the amount of specific solute coming to a permeated liquid to the amount of the specific solute supplied to the membrane can be an indicator. The recovery rate under the condition as shown by Examples of the present application is preferred to be more than 95% which is presumed to be a practical recovery. When it is 95% or less, there is much loss of a solute (such as protein) due to the clogging or the like resulting in a decrease of the yield rate in a purifying process. In the constant rate filtration, the fact whether a filtration is suitably conducted or not is judged based on, for example, whether how much amount of a solute can be recovered (a product of the filtrate amount and the filtrate concentration) until a designed pressure for operation is achieved. The recovery amount of a solute under the condition as shown in Examples of the present application is preferred to be 500 g/m$^2$ or more. When the recovery amount of a solute is less than 500 g/m$^2$, a rise in pressure due to the clogging is significant and no sufficient recovery amount can be achieved. More preferably, it is 800 g/m$^2$ or more.

The porous hollow fiber membrane of the present invention has an excluding ability, by means of filtration, for virus contained in water such as a protein solution. As to a practical excluding ability for virus, it is preferred to be more than 4 (removing rate: more than 99.99%) in terms of LRV value wherein small virus is an object. Thus, when the membrane has LRV of 4, it means that, when 10,000 (1×10$^4$) viruses are present in a liquid to be treated, the membrane has an ability of trapping nearly all of them. In order to secure the higher property, LRV is more preferred to be 4.5 or more and further preferred to be 5.0 or more. Incidentally, with regard to the virus, even when highly safe virus (such as bacteriophage which is a bacteria (such as *Escherichia coli*) infectious virus) is used instead of human infectious pathogenic virus, it can also be utilized as the entirely same evaluating indicator. When broad applicability and safety as evaluation of industrial products are taken into consideration, LRV using bacteriophage is adaptable therefor.

It goes without saying that contamination of the filtrate with an eluate of the hollow fiber membrane is to be avoided if at all possible. With regard to a filtration membrane for industrial process used in the manufacture of pharmaceuticals, there is no clear standard for an eluate while, in the similar use, a standard for chemical characteristic of a membrane for artificial kidney as a medical instrument (Test of Standard for Approval of Artificial Kidney; at the time of 2012, this standard had been abrogated) can be conceived as a useful standard. In this standard, there is a norm by ultraviolet absorption for 220 nm to 350 nm wavelength of the extract prepared from the membrane and the fact that the maximum absorbance between those wavelengths is 0.1 or less is taken as a norm in terms of safety. In the membrane of the present invention, it is also preferred to be in accordance with the norm set for a medical instruments. Accordingly, it is preferred that the absorbance of an extract measured by a method of Examples is 0.1 or less. It is more preferred to be 0.07 or less. A polyether sulfone and a VA copolymer used as constitutions of the present invention as shown in Examples are ultraviolet absorbing substances and can be effective indicators for judging the elution thereof.

Outline of the method for manufacturing the porous hollow fiber membrane according to the present invention is exemplified as hereunder. The hydrophobic polymer and the first hydrophilic polymer are mixed and dissolved in a solvent to which a non-solvent may be added upon necessity followed by defoaming and the resulting one is used as a solution for membrane preparation. The resulting solution for membrane preparation is discharged from a ring-shaped part of a tube-in-orifice nozzle while a core liquid is discharged from a central part simultaneously followed by introducing into a coagulation bath via an air running part (air gap part) to form a hollow fiber membrane (dry-and-wet spinning method). It is washed with water, wound around a spool, washed and dried followed by subjecting to a coating treatment using the second hydrophilic polymer.

With regard to a solvent used for a solution for membrane preparation, anything may be broadly used so far as it is a good solvent for a polysulfone-type polymer and a VA copolymer used therefor such as N-methyl-2-pyrrolidone (hereinafter, it may be abbreviated as NMP), N,N-dimethylformamide (hereinafter, it may be abbreviated as DMF), N,N-dimethylacetamide (hereinafter, it may be abbreviated as DMAc), dimethyl sulfoxide (hereinafter, it may be abbreviated as DMSO) or ε-caprolactam. Among them, preferred ones are NMP, DMF & DMAc, and more preferred one is NMP.

It is also possible to add a non-solvent for a hydrophobic polymer and for a hydrophilic polymer to a solution for membrane preparation. Examples of the non-solvent used therefor include ethylene glycol (hereinafter, it may be abbreviated as EG), propylene glycol (hereinafter, it may be abbreviated as PG), diethylene glycol (hereinafter, it may be abbreviated as DEG), triethylene glycol (hereinafter, it may be abbreviated as TEG), polyethylene glycol (hereinafter, it may be abbreviated as PEG), glycerol and water. Among them, ether polyol such as DEG, TEG or PEG is preferred, and TEG is more preferred when a polymer of a polysulfone type and a hydrophilizing agent of a polyvinylpyrrolidone type are used. Incidentally, an ether polyol in the present invention means a substance having at least one ether bond and two or more hydroxyl groups in its structure.

The ratio of the solvent to the non-solvent in a solution for membrane preparation is an important factor for the control of the phase separation (coagulation) in a spinning step. As a condition for obtaining the membrane structure of the present invention, it is preferred that the non-solvent is in the same amount as or in somewhat excessive amount to the solvent. To be more specific, the ratio by weight of solvent/non-solvent is preferred to be from 25/75 to 50/50. When the amount of the solvent is less than that, coagulation is apt to proceed and the membrane structure becomes too dense whereby the permeation property lowers. Accordingly, it is possible to obtain a desired flux or protein permeation. When the amount of the solvent is more than that, progress of the phase separation is excessively suppressed, pores in large diameter are apt to be generated and there is a possibility of resulting in the lowering of separation property and strength. That is not preferred.

Although there is no particular limitation for the concentration of the polysulfone-type polymer in the solution for membrane preparation so far as the preparation of the membrane from the solution is possible, it is preferred to be 20 to 40% by weight. In order to achieve a high permeation property, the concentration of the polysulfone-type polymer is preferred to be low but, when it is extremely low, there is a possibility of resulting in lowering of the strength and deterioration of the separation property. On the other hand, in order to surely trap the very small substances such as virus, it is necessary that hollow rate of the dense layer is made as low as possible whereby the trapping property is made surer. Therefore, it is more preferred that the concentration of a polysulfone-type polymer is higher. However, when the concentration of the polysulfone-type polymer is made high, it sometimes happens that the membrane as a whole results in a too dense structure how intensively the membrane preparation condition may be controlled.

Amount of the VA copolymer to be added to a solution for membrane preparation is preferred to be as much as possible in order to control distribution of pore size and asymmetry of membrane in such a manner that the suppressive component such as virus is highly trapped while the recovery component such as protein is highly permeated. As a result of solubility and viscosity of the solution for membrane preparation and residual amount in the membrane are investigated, concentration of the VA copolymer in the solution for membrane preparation is preferred to be 5 to 15% by weight and more preferred to be 6 to 12% by weight. When the adding amount of the copolymer is less than that, control of the membrane structure and residual amount in the membrane become insufficient whereby the property lowers. When it is more than that, phase separation (coagulation) of the solution for membrane preparation is apt to proceed excessively and the operability upon the manufacture of the hollow fiber membrane (filtration of the spinning dope through a filter and fiber breakage) becomes bad. In addition, diffusion of the polymer in the phase separation significantly lowers whereby that is not preferred for the formation of the membrane structure which is favored in the present invention and also for the residual amount of the VA copolymer.

The solution for membrane preparation can be obtained by mixing of polysulfone-type polymer, VA copolymer, solvent and non-solvent followed by stirring and dissolving. At that time, an excessive heating has a risk of causing decomposition of polymer and phase separation at high temperature of spinning dope which is particular to the present invention. Heating temperature is preferred to be 30 to 80° C. The solution for membrane preparation is preferred to be prepared together with filling the inert gas since VA copolymer tends to result in oxidative degradation affected by oxygen in the air. Examples of the inert gas include nitrogen and argon and the use of nitrogen is preferred. At that time, it is preferred that the residual oxygen concentration in a dissolving tank is 3% or less.

With regard to the composition of the core liquid used in the preparation of the hollow fiber membrane, it is preferred to use a liquid containing, as the main component (s), the solvent and/or the non-solvent contained in the solution for membrane preparation. However, when the core liquid contains only a solvent contained in the solution for membrane preparation, coagulation on the lumen wall surface is excessively suppressed whereby it is impossible to give a preferred surface structure. Accordingly, it is preferred to use any of a mixed liquid of solvent and non-solvent, non-solvent only, a mixed liquid of solvent and water, a mixed liquid of non-solvent and water and a mixed liquid of solvent, non-solvent and water. It is more preferred to prepare a mixed liquid containing solvent and non-solvent in the same ratio as that of solvent/non-solvent in the solution for membrane preparation followed by diluting with water. At that time, the concentration of the organic component is made 70 to 100% by weight. When the amount of the organic component is less than 70% by weight, coagulation is apt to proceed and the structure of inner side of the membrane becomes too dense whereby the permeation property lowers.

It is preferred that the composition of the outer coagulating liquid uses a mixed liquid of water with the solvent and non-solvent contained in a solution for membrane preparation. At that time, the rate of the solvent to the non-solvent is preferably same as the rate of solvent/non-solvent in the solution for membrane preparation. Preferably, the solvent and non-solvent which are the same as those used for the solution for membrane preparation are mixed in the same rate as that in the solution for membrane preparation and water is added thereto for dilution. In order to achieve a shape wherein the outer layer has the dense layer which is the structural characteristic of the porous hollow fiber membrane of the present invention, it is preferred that the concentration of an organic component in a core liquid is higher than that in the outer coagulating liquid. Amount of water in the outer coagulating liquid is 20 to 70% by weight. When the amount of water is more than that, coagulation is apt to proceed and the membrane structure becomes too dense whereby the permeation property lowers. When the amount of water is less than that, progress of the phase separation is excessively suppressed and pores in large diameter are apt to be formed whereby there is a high possibility of resulting in the lowering of separation property and strength. When temperature of the outer coagulating liquid is low, coagulation is apt to proceed and the membrane structure becomes too dense whereby the permeation property may lower. When it is high, progress of phase separation is excessively suppressed and pores in large diameter are apt to be formed whereby there is a high possibility of resulting in the lowering of separation property and strength. Accordingly, the temperature is 20 to 60° C.

One of the factors for controlling the membrane structure is the nozzle temperature. When the nozzle temperature is low, coagulation is apt to proceed and the membrane structure becomes too dense whereby the permeation property lowers. When the nozzle temperature is high, progress of the phase separation is excessively suppressed and pores in large diameter are apt to be formed whereby there is a high possibility of resulting in the lowering of separation property and strength. Accordingly, preferable nozzle temperature is 40 to 80° C.

A solution for membrane preparation extruded from a tube-in-orifice nozzle together with a core liquid is introduced into an outer coagulating bath via the air gap part. In the outer coagulating bath, the resulting hollow fiber membrane contacts with the outer coagulating liquid, together with the progress of coagulation from the core liquid, in such a state that the coagulation from outside is suppressed to some extent. During course of passing through the outer coagulating liquid, coagulation of the hollow fiber membrane completely finishes and the structure is determined followed by being drawn up.

Although there is no particular limitation for the membrane-preparation velocity (spinning speed) so far as a hollow fiber membrane without defect is obtained and the productivity is ensured, it is preferably 5 to 40 m/minute. When the spinning speed is lower than that, the productivity may lower. When the spinning speed is higher than that, it is difficult to secure the above-mentioned spinning conditions or, particularly, the retention time at the air gap part.

The porous hollow fiber membrane of the present invention has such a structure wherein only the outer layer has a dense layer. The structure as such can be easily obtained when the membrane preparation condition is made optimal by taking the above-mentioned preferred conditions such as composition of solution for membrane preparation, composition of core liquid, composition of outer coagulating liquid, various temperature controls and retention time are into consideration.

The porous hollow fiber membrane is obtained via a washing step after preparing the membrane. Although there is no particular restriction for the method of washing the hollow fiber membrane, it is preferred in view of washing effect, safety and simplicity that the prepared hollow fiber membrane is just made to run in a washing bath filled with warm water online and then wound. Temperature of the warm water used at that time is preferably from room temperature to 80° C. When the temperature is lower than that, there is a high possibility that a washing effect is not sufficient while, when it is higher than that, energy cost becomes high due to online running.

After preparing the membrane, the hollow fiber membrane obtained via an online washing is uniformly cut in an appropriate length and tied up to make into a bundle shape. For a purpose of removing the liquid existing in the hollow part, the bundle in a standing state is allowed to stand for 30 minutes to 2 hours. When it is shorter than 30 minutes, removal of the liquid in the hollow part becomes insufficient, so it is not preferred. When it is allowed to stand for more than 2 hours, the porous hollow fiber membrane becomes dry or the bundle is flattened due to its own weight during a standing state, so it is not preferred.

The above bundle wherefrom the inner liquid in the hollow part is removed is then subjected to a further washing step wherein warm water is infused from lower area of the bundle in a standing state to make into an immersed state and then water is discharged therefrom. Such a method is repeated so that the solvent and the non-solvent are completely discharged from the inner and outer sides of the hollow part and from the inner area of the porous hollow fiber membrane. Temperature of the warm water is preferred to be 70° C. to 95° C. and more preferred to be 75° C. to 90° C. For washing out the solvent and the non-solvent, water of high temperature is efficient but it is difficult to constantly keep the temperature of higher than 95° C. being near the boiling point, so it is not preferred. When the temperature is lower than 70° C., the washing effect is not sufficient, so it is not preferred. Immersion of the bundle using the water of high temperature and removal of the liquid therefrom are preferred to be conducted repeatedly and, to be more specific, repetition for 5 to 20 times is preferred due to its good washing effect. When it is less than 5 times, the washing effect is not sufficient, so it is not preferred. In addition, even when it is repeated for more than 21 times, there is no change in the washing effect and the manufacturing cost becomes high, so it is not preferred.

It is preferred that, after the above-mentioned washing treatment, the porous hollow fiber membrane of the present invention is treated with hot water of high pressure. To be more specific, it is preferred to be set in a high-pressure steam sterilizer in a state of being immersed in water followed by subjecting to a treatment under the usual high-pressure steam sterilizing condition with the treating temperature of 120 to 150° C. and the treating time of 20 to 120 minutes. As a result of treating with high-pressure hot water, the amount of the VA copolymer existing in the porous hollow fiber membrane is adjusted. In the porous hollow fiber membrane of the present invention, a blend of a polysulfone type polymer with a VA copolymer is a constituting component but they are not bound by means of chemical bond but are presumed to be present in the membrane by entangling of the polymers. To be more specific, the fundamental skeleton is composed of a polysulfone type polymer which is a hydrophobic polymer and it is likely to exist in the membrane in such a state that the VA copolymer which is a hydrophilic polymer is entangled with the fundamental skeleton. However, there is molecular distribution in the copolymer and lowly molecular ones also exist and, in addition, even a highly molecular one is apt to be easily dropped out from the membrane when its entangling with a polysulfone type polymer is insufficient. Since it causes a problem when such a substance which is in a state of being apt to be dropped out is eluted during the use of the porous hollow fiber membrane of the present invention, it is necessary to wash out and remove the component which is apt to be eluted. When the treating temperature is lower or the treating time is shorter than the above-mentioned ranges, the removal of excessive VA copolymer and the optimization of the existing state become insufficient resulting in inconveniences such as the changes in membrane characteristics with elapse of time and the contamination of a solution to be treated due to the elution in actual use. When the treating temperature is higher or the treating time is longer than the above-mentioned ranges, lowering of separation property and strength are resulted due to the breakage of the layer structure, the excessive extraction of the copolymer, etc.

The porous hollow fiber membrane wherefrom an excessive VA copolymer is removed by means of a high pressure hot water treatment is dried and sent to the next coating treatment step using a cellulose type polymer. With regard to a drying method, a commonly used drying method such as drying with air, drying in vacuo, drying with hot air and drying by microwave may be broadly used. In such a view that large quantity of hollow fiber membrane can be efficiently dried using a simple device, drying with hot is preferably utilized. When the above treatment with high pressure hot water is conducted before drying, changes in the membrane characteristics due to the drying with hot air can be also suppressed. Although there is no particular limitation for the temperature of hot air in the drying using hot air, it is preferred to be 25 to 100° C. and more preferred to be 30 to 80° C. When the temperature is lower than that, long time is needed until being dried while, when it is higher than that, cost for energy becomes high due to the generation of hot air, so any of them is not preferred. Temperature of hot air is preferred to be lower than the temperature for the above treatment with hot water.

The porous hollow fiber membrane prepared as above is then immersed in a coating solution consisting of an aqueous solution of lower alcohol in which a cellulose type polymer which is the second hydrophilic polymer is dissolved whereby the cellulose type polymer is adhered onto the membrane surface including the pore surface. Examples of the lower alcohol include ethanol and 2-propanol. The aqueous solution of lower alcohol also contributes in the washing of the porous hollow fiber membrane and it is now possible to remove the VA copolymer which still cannot be fully removed by the above treatment with high pressure hot water. Thus, when it is preferable to use an aqueous solution of lower alcohol is used, there is an advantage that the removal of excessive VA copolymer and the coating treatment can be conducted simultaneously.

With regard to a coating solution, it is preferable to use an aqueous solution containing 0.1 to 1.0% by weight and preferably 0.3 to 0.7% by weight of a cellulose type polymer as well as 10 to 30% by weight and preferably 15 to 25% by weight of 2-propanol. When the concentration of the cellulose type polymer is lower than the above range, it is insufficient to impart the hydrophilicity to the porous hollow fiber membrane. On the contrary, when it is higher than the above range, viscosity of the aqueous solution becomes high whereby the whole membrane cannot be uniformly made hydrophilic. In addition, when the concentration of the lower alcohol is adjusted to the above range, it is possible to suppress an excessive dropout of the VA polymer by the coating solution. With regard to the treating time, it is sufficient that the porous hollow fiber membrane is immersed in the above-mentioned aqueous solution for about 30 minutes.

After the above treatment finishes, the porous hollow fiber membrane is taken out and immersed in warm water to conduct a heating treatment. When it is conducted under a reduced pressure condition of from (ordinary pressure −0.06 MPa) to (ordinary pressure −0.08 MPa) at that time, the warm water can be permeated even into the inner part of the pores. As a result of such a treatment, the coat of the cellulose type polymer can be made stable. In the cellulose type polymer in an aqueous solution of ordinary room temperature, hydroxyl group in cellulose forms a hydrogen bond with water molecule or with other hydroxyl group in cellulose molecule and the interaction with the substrate to be coated is weak. By the treatment with hot water, such a hydrogen bond is once cut, and a conformation change and rearrangement are caused so as to enhance an interaction with the hydrophobic substrate or with the first hydrophilic polymer whereby a stable coat can be formed. Temperature of the warm water is preferred to be 60° C. to 95° C. and more preferred to be 80° C. to 95° C. Time for immersion is preferred to be 10 to 90 minutes and more preferred to be 30 to 60 minutes. When the porous hollow fiber membrane prepared as such is subjected to a drying treatment once again under the above-mentioned condition, the porous hollow fiber membrane of the present invention can be obtained.

EXAMPLES

As hereunder, the effect of the present invention will be illustrated by referring to Examples although the present invention is not limited thereto. Incidentally, the evaluating methods in the following Examples are as shown below.

1. Preparation of Micromodule

A hollow fiber membrane was cut in the length of about 30 cm, both ends thereof were put into a Luer Tip to make into a loop shape, adjustment was conducted for making the both ends of the hollow fiber membrane open and a tip part is adhered using a hot melt resin. Hollow fiber membrane numbers were appropriately set so that the membrane area based on inner diameter became 1.0 to 10 cm$^2$.

2. Measurement of Inner Diameter, Outer Diameter and Membrane Thickness of Hollow Fiber Membrane A hollow fiber membrane was observed in its dried state. Inner diameter, outer diameter and membrane thickness of the hollow fiber membrane were obtained as follows: The hollow fiber membrane in appropriate numbers were passed into a pore of 3 mm diameter formed in the center of a slide glass to such an extent that the membrane was not fallen therethrough and cut using a razor on the upper and lower sides of the slide glass. The resulting cross-sectional sample of the hollow fiber membrane was subjected to measurement of short and long diameters of the cross section of the hollow fiber membrane using a projector (Nikon-V-12A). Short and long diameters in two directions were measured for each cross section of the hollow fiber membrane. Arithmetic mean value of each of them was used as inner diameter and outer diameter for one cross section of the hollow fiber membrane while membrane thickness was calculated as [(outer diameter−inner diameter)/2]. Five cross sections were subjected to the same measurement and the mean values thereof were adopted as inner diameter, outer diameter and membrane thickness.

3. Calculation of Membrane Area

Membrane area of the module was determined on the basis of the diameter of the inside of the hollow fiber membrane. The membrane area A [m$^2$] can be calculated by the following formula.

$$A = n \times \pi \times d \times L$$

In the formula, n is numbers of the hollow fiber membrane, π is ratio of the circumference of a circle to its diameter, d is inner diameter [m] of the hollow fiber membrane and L is an effective length [m] of the hollow fiber membrane in the module.

4. Measurement of Pure Water Flux

Pure water was filled in a pressure-resisting chamber and connected to a micromodule. Water temperature was controlled at 25° C. and filtration was conducted to the direction from inside to outside of the hollow fiber membrane with a filtration pressure of 1.0 bar. The filtrate during the initial 30 seconds was discarded and, after that, the filtrate was recovered during 2 minutes and its volume was measured. The pure water flux [L/(h·m$^2$·bar)] was calculated by the following formula from filtration time t [h], filtration pressure P [bar], membrane area of the module A [m$^2$] and amount of the filtrate V [L].

$$\text{Pure water flux} = V/t/A/\Delta P$$

5. Observation of a Fractionated Layer of 20 nm

A commercially available homogeneous solution of 20-nm gold colloid (manufactured by Sigma) (containing a small amount of citric acid; neither stabilizer nor dispersing agent was contained therein) (6 ml) and 3 ml of a 2.0% aqueous solution of bovine serum albumin (manufactured by Nakarai Tesque) were mixed, 3 ml of a 0.4% aqueous solution of glutathione (a reduced type) was added thereto and the resulting gold colloid solution was subjected to a constant pressure filtration with a filtration pressure of 1 bar. After the filtration, another filtration was conducted under the same condition using the same volume of pure water as that of the filtrated gold colloid solution, then the hollow fiber membrane was dried with air and the membrane after the drying was cut using a razor in a vertical or parallel direction to an axis so that the cross section can be observed. After it was fixed on a sample stand in such a manner that the cross section thereof turns directly upward, residual state of gold colloid on the cross section was observed under an optical microscope. When it is difficult to cut the cross section because of the reasons that, for example, the sample is thin, it is also acceptable that the hollow fiber membrane is embedded in resin, cut in cross section and subjected to the observation. When the gold colloid is trapped in any site of the cross sectional part of the membrane (particularly at the site wherein the membrane is dense and becomes the narrowest pore for separation), trapping is resulted in such a site (layer) in a concentrated manner and coloring in red is achieved whereby an observation of the dense layer is possible.

6. Measurement of Amount of the Constituting Components Contained in the Membrane (1) Analysis of Whole Membrane (NMR Method)

The hollow fiber membrane (10 mg) was dissolved in DMSO-d6 and an H-NMR spectrum was measured at 40° C. Based on the H-NMR spectrum solely measured for each of the constituting components of the hollow fiber membrane, amount of a hydrophilic polymer was calculated from the peak of the related functional group.

(2) Analysis of the Area Near the Surface Layer of the Membrane (IR Method)

An IR spectrum of outer surface of the hollow fiber membrane was measured (once-reflection ATR method; diamond: 45°). Each of the constituting components of the hollow fiber membrane was measured solely. The IR analysis result was corrected using the confirmed peak analysis and the calibration curve prepared by NMR, and the amount of the hydrophilic polymer was calculated.

(3) Ratio of IR Value to NMR Value

Ratio of IR value/NMR value=IR value (outer side)÷NMR value (whole)

When this ratio is 0.9 to 1.1, the hydrophilic polymer is judged to be homogeneously distributed.

7. Breaking Strength

Measurement was conducted using Tensilon UTM II manufactured by Toyo Baldwin.

The hollow fiber membrane in a dry state was measured under the conditions wherein tensile speed was 100 mm/min and distance between chucks was 100 mm.

8. Burst Strength (Burst Pressure)

A module wherein three hollow fiber membranes were bundled in a loop shape was prepared and set at a pressure tester which was durable against the pressurization up to 1.0 MPa. The hollow fiber part was immersed in water and pressurization was done with air from the hollow part side and the pressure when the air began to leak was measured.

9. Measurement of clearance index for a bacteriophage øX174

(1) Preparation of a Phage Liquid for the Test

Albumin from bovine serum (Product No. A2153) commercially available from Sigma Aldrich Japan was dissolved in phosphate buffer so as to make the concentration 0.1% by weight whereby a 0.1% by weight solution of BSA (hereinafter, it will be just called a BSA solution) was obtained. A freeze-stored and concentrated liquid containing ø X 174 (NBRC103405) (titer: 1 to $10 \times 10^9$ pfu/mL) was thawed and diluted to an extent of 100 times using the BSA solution. It was further filtrated through a membrane filter of 0.1 μm pore size to remove the coagulated component, etc. and used as a phage liquid for the test.

(2) Filtration Test Using the Phage Liquid for the Test

The phage liquid was subjected to a constant pressure filtration with a filtration pressure of 2 bar from the inside to the outside of the hollow fiber membrane using a micromodule. The flowing-in pressure was made to be measured at the introducing side of the liquid. Filtration was conducted until 200 L of the filtrate per $m^2$ of the hollow fiber membrane area was obtained.

(3) Measurement of the Phage Liquid for the Test and the Phage Titer of the Filtrate

*Escherichia coli* (NBRC13898) was suspended in a 10 mM aqueous $MgSO_4$ solution so that the absorbance at 660 nm was made 4.0 (hereinafter, it will be called as *E. coli* liquid). Further, agar medium and top agar were prepared and warmed at 50° C. Particularly for top agar, careful attention was paid for keeping its fluidity. A liquid (10 μL) wherein the phage liquid for the test was appropriately diluted by the BSA solution was mixed with the 50 μL of the *E. coli* liquid followed by incubating at 37° C. for 20 minutes so as to infect *E. coli* with the phage. After completion of the incubation, all of the mixed liquid was mixed with 3 mL of top agar and the whole amount was developed onto an agar medium. After the top agar was completely solidified on the agar medium, incubation was conducted at 37° C. for 2 to 4 hours. After completion of the incubation, the plaque numbers on the agar medium were counted and, taking the diluting rate into consideration, the titer of the phase liquid for the test (hereinafter, it will be abbreviated as Tpre) [pfu/ml] was calculated. Phage titer of the filtrate (hereinafter, it will be abbreviated as Tpost) was also obtained by the same means.

(4) Calculation of Phage Clearance Index of the Hollow Fiber Membrane

A phage clearance index of the hollow fiber membrane was calculated by the following formula. In the formula, Tpre [pfu/mL] means the titer of the phage liquid for the test introduced into the hollow fiber membrane for the evaluation and Tpost [pfu/mL] means the titer of the filtrate obtained by filtrating the phage liquid for the test through a hollow fiber membrane for the test.

Phage clearance index [LRV]=$\log_{10}$(Tpre/Tpost)

When the LRV value is more than 4 (removing rate of more than 99.99%), the removing rate for ø x 174 phage is judged to be sufficiently high and can be a substitute indicator for the removing ability of small virus of about 20 nm size being the similar size.

Tpre of the phage used here for the evaluation is conducted under the titer condition of $3.2 \times 10^5$ [pfu/mL] or more. When Tpost at that time is 1 [pfu/mL], then LRV=5.5. In addition, when Tpost is 0 [pfu/mL] or, in other words, in the case of complete removal (in such a case wherein no plaque formation is noted), LRV is interpreted as >5.5 (more than 5.5). As such, the value corresponding to the complete removal of phage clearance in the plaque test varies depending upon Tpre. In the present test, evaluation is conducted under the Tpre condition by which >5.5 can be surely judged and all of the cases wherein LRV corresponding to the complete removal is more than 5.5 are regarded as >5.5.

10. Constant Pressure Filtration of Immunoglobulin Solution

Dulbecco PBS (-) powder "Nissui" commercially available from Nissui Seiyaku (9.6 g) was dissolved in distilled water to make the total volume 1000 mL whereby PBS was obtained. Kenketsu Venoglobulin IH Yoshitomi commercially available from Tanabe-Mitsubishi Pharmaceutical was diluted to an extent of five-fold using the PBS to prepare a 1.0% solution of human immunoglobulin preparation for intravenous injection (pH 6.8) (hereinafter, it may be abbreviated as IVIG). The 1.0% IVIG was filled in a chamber, a micromodule was connected thereto and setting was done in such a state that filtration from inside to outside of the hollow fiber was made possible. Temperature of the liquid to be evaluated was controlled to 25° C. and a constant pressure filtration was conducted with a filtration pressure of 1.0 bar. Filtration time and filtrated amount were monitored with intervals of predetermined time and the relation between the filtration time and the filtrated amount was measured. The filtration was carried out until 50 L of filtrate per 1 $m^2$ of the sample was achieved. IVIG concentration in the recovered filtrate was measured and the recovery rate was calculated using the ratio to the concentration of the original liquid {[(concentration of filtrate)/(concentration of original liquid)]×100}. When the recovery rate is 95% or more, it is judged that a good recovery is achieved.

11. Constant Rate Filtration of Immunoglobulin Solution

A 1.0% solution of human immunoglobulin for intravenous injection (pH 6.8) (hereinafter, it may be abbreviated as IVIG) prepared in the same manner as in the above 10 was filled in a syringe and set to a syringe pump. A micromodule was connected thereto to result in a state wherein the filtration from inside to outside of the hollow fiber was possible. Temperature of the liquid to be evaluated was controlled to 25° C., filtration was conducted at a constant filtration rate (120 L/$m^2$/hr) and a constant rate filtration was conducted until the filtration pressure reached 3 bar. Filtration pressure and filtrated amount were monitored with intervals of predetermined time and the relation between the filtration time and the filtrated amount and a rising tendency of the filtration pressure were measured. The total liquid amount which was filtrated until the filtration pressure reached 3 bar was determined. In addition, the IVIG concentration in the filtrate was measured, the IVIG amount which could be filtrated and recovered was calculated by the same method as mentioned above. The total weight of the recovered IVIG was calculated from the product of the IVIG concentration in the filtrated/recovered liquid and the amount of the filtrate and the value (g/$m^2$) calculated by dividing the above weight by the membrane area was evaluated as a recovered amount. When the recovery amount which was filtrated until the filtration pressure reached 3 bar was 500 g/$m^2$ or more, it is judged that the hollow fiber membrane has a sufficiently high recovering ability.

12. UV Absorbance (220 to 350 nm)

A hollow fiber membrane bundle in a dry state (1 g) was weighed, immersed in 100 g of RO water and extracted at 132° C. for 20 minutes using an autoclave. Absorbance within a wavelength range of 220 to 350 nm of the extract was measured using a spectrophotometer (U-3000 manufactured by Hitachi) and the maximum absorbance within this wavelength range was evaluated as a solute. From the fact that a copolymer of vinylpyrrolidone with vinyl acetate has an absorption derived from C=O, degree of elution thereof can be evaluated.

Example 1

PES (Ultrason (registered trade mark) 6020P manufactured by BASF) (27% by weight), 9% by weight of VA6/4 (Luvitec (registered trade mark) VA 64) manufactured by BASF, 28.8% by weight of NMP manufactured by Mitsubishi Chemical and 35.2% by weight of TEG manufactured by Mitsui Chemical were mixed and dissolved at 55° C. to give a homogeneous solution. Further, this solution was defoamed under tightly sealing in vacuo and the resulting solution was used as a solution for membrane preparation. The above solution was discharged from a ring-shaped part of a tube-in-orifice nozzle while, from a core part thereof, a mixed liquid of 42.75% by weight of NMP, 52.25% by weight of TEG and 5% by weight of RO water was discharged as a core liquid and, after passing through an air gap, it was introduced into a coagulation bath which was filled with an outer coagulation liquid consisting of a mixed liquid of 27% by weight of NMP, 33% by weight of TEG and 40% by weight of RO water. At that time, nozzle temperature was set at 50° C. and outer coagulation liquid temperature was set at 30° C. After being pulled out from the coagulation bath, it was made to run in a washing bath of 55° C. to conduct an online washing and, after that, it was wound up using a winding machine.

The wound-up hollow fiber membranes were made into a bundle of 40 cm length consisting of 5000 membranes. For a purpose of removing the core liquid therefrom, the bundle in a standing state was allowed as it was for 30 minutes. After that, it was immersed in RO water of 85° C. in a straightly standing state to subject to a washing treatment. The liquid in the warm water tank was exchanged for five times so as to repeat the washing treatment. After that, the bundle being still in a wet state was quickly immersed in warm water of 40° C. placed in a high-pressure steam sterilizing machine and subjected to a treatment with hot water at high pressure under the condition of 140° C. for 20 minutes. After that, it was dried by means of microwave with the temperature in the device of 35° C. The high-pressure steam treatment and drying were repeated for three times.

The resulting bundle was immersed in a solution containing 20% by weight of 2-propanol manufactured by Nakarai Tesque, 0.5% by weight of HPC (weight-average molecular weight: 50000) manufactured by Nippon Soda and 79.5% by weight of RO water at 25° C., the container was tightly closed and then quickly depressurized down to −0.07 MPa. After being allowed to stand for 20 minutes, the container was returned to ordinary pressure, and then the bundle was taken out therefrom. The bundle was allowed to stand for 5 minutes in a standing state in order to remove the treating liquid therefrom. After that, it was immersed in RO water of 80° C. in a straightly standing state and a gelling treatment was conducted for 1 hour. After that, drying by means of microwave was conducted with the temperature in the device of 35° C. whereby a bundle was prepared.

In the resulting hollow fiber membrane, the inner diameter was 195 μm and the membrane thickness was 59 μm. When a micromodule was prepared and the pure water flux was measured, it was found to be 190 L/($m^2$·h·bar). From the observation of an SEM image and of a cross section after filtration of gold colloid, a dense layer was noted on the outer side only. Further, the amount of a VA copolymer existing in the whole membrane (NMR measurement) and the amount of a VA copolymer existing near the outer surface (IR measurement) were 7.6% by weight and 7.1% by weight, respectively and the ratio of IR/NMR was 0.93. Accordingly, it is likely that the VA copolymer was homogeneously dispersed. The amount of HPC was 1.3% by weight. The breaking strength and burst pressure of the hollow fiber membrane were 67 g/filament and >9 bar, respectively. Further, in the constant pressure filtration of IVIG, the recovery rate was >98%. Also, in the constant rate filtration of IVIG, 2750 g/m$^2$ of IVIG could be recovered. As a result of measurement for a virus removing ability using øX-174, the LRV value was >5.5. Further, the maximum value of the UV absorbance (220 to 350 nm) was 0.051. The above results are shown in Table 1.

Example 2

PES (30% by weight), 6% by weight of VA6/4, 28.8% by weight of NMP and 35.2% by weight of TEG were mixed and dissolved at 55° C. to give a homogeneous solution. Further, this solution was defoamed and the resulting solution was used as a solution for membrane preparation. The above solution was discharged from a ring-shaped part of a tube-in-orifice nozzle while, from a core part thereof, a mixed liquid of 40.5% by weight of NMP, 49.5% by weight of TEG and 10% by weight of RO water was discharged as a core liquid and, after passing through an air gap, it was introduced into a coagulation bath which was filled with an outer coagulation liquid consisting of a mixed liquid of 24.75% by weight of NMP, 30.25% by weight of TEG and 45% by weight of RO water. At that time, nozzle temperature was set at 55° C. and outer coagulation liquid temperature was set at 30° C. After being pulled out from the coagulation bath, it was made to run in a washing bath of 55° C. to conduct an online washing and, after that, it was wound up using a winding machine.

By subjecting the wound-up hollow fiber membrane to the same treatment as in the step shown in Example 1, the aimed bundle was prepared.

In the resulting hollow fiber membrane, the inner diameter was 185 μm and the membrane thickness was 55 μm. When a micromodule was prepared and the pure water flux was measured, it was found to be 170 L/(m$^2$·h·bar). From the observation of an SEM image and of a cross section after filtration of gold colloid, a dense layer was noted on the outer side only. Further, the amount of a VA copolymer existing in the whole membrane (NMR measurement) and the amount of a VA copolymer existing near the outer surface (IR measurement) were 7.1% by weight and 7.0% by weight, respectively and the ratio of IR/NMR was 0.99. Accordingly, it is likely that the VA copolymer was homogeneously dispersed. The amount of HPC was 1.2% by weight. The breaking strength and burst pressure of the hollow fiber membrane were 78 g/filament and >9 bar, respectively. Further, in the constant pressure filtration of IVIG, the recovery rate was >98%. Also, in the constant rate filtration of IVIG, 950 g/m$^2$ of IVIG could be recovered. As a result of measurement for a virus removing ability using øX-174, the LRV value was >5.5. Further, the maximum value of the UV absorbance (220 to 350 nm) was 0.036. The above results are shown in Table 1.

Example 3

PES (24% by weight), 12% by weight of VA6/4, 38.4% by weight of NMP and 25.6% by weight of TEG were mixed and dissolved at 65° C. to give a homogeneous solution. Further, this solution was defoamed and the resulting solution was used as a solution for membrane preparation. The above solution was discharged from a ring-shaped part of a tube-in-orifice nozzle while, from a core part thereof, a mixed liquid of 54% by weight of NMP, 36% by weight of TEG and 10% by weight of RO water was discharged as a core liquid and, after passing through an air gap, it was introduced into a coagulation bath which was filled with an outer coagulation liquid consisting of a mixed liquid of 18% by weight of NMP, 12% by weight of TEG and 70% by weight of RO water. At that time, nozzle temperature was set at 55° C. and outer coagulation liquid temperature was set at 40° C. After being pulled out from the coagulation bath, it was made to run in a washing bath of 55° C. to conduct an online washing and, after that, it was wound up using a winding machine.

By subjecting the wound-up hollow fiber membrane to the same treatment as in the step shown in Example 1, the aimed bundle was prepared.

In the resulting hollow fiber membrane, the inner diameter was 200 μm and the membrane thickness was 59 μm. When a micromodule was prepared and the pure water flux was measured, it was found to be 135 L/(m$^2$·h·bar). From the observation of an SEM image and of a cross section after filtration of gold colloid, a dense layer was noted on the outer side only. Further, the amount of a VA copolymer existing in the whole membrane (NMR measurement) and the amount of a VA copolymer existing near the outer surface (IR measurement) were 7.6% by weight and 7.6% by weight, respectively and the ratio of IR/NMR was 1.0. Accordingly, it is likely that the VA copolymer was homogeneously dispersed. The amount of HPC was 1.7% by weight. The breaking strength and burst pressure of the hollow fiber membrane were 52 g/filament and >9 bar, respectively. Further, in the constant pressure filtration of IVIG, the recovery rate was 97%. Fractional molecular weight was 150000 to 1000000. Also, in the constant rate filtration of IVIG, 876 g/m$^2$ of IVIG could be recovered. As a result of measurement for a virus removing ability using øX-174, the LRV value was >5.5. Further, the maximum value of the UV absorbance (220 to 350 nm) was 0.062. The above results are shown in Table 1.

Example 4

PES (20% by weight), 6% by weight of VA6/4, 37% by weight of NMP and 37% by weight of TEG were mixed and dissolved at 65° C. to give a homogeneous solution. Further, this solution was defoamed under tightly sealing in vacuo and the resulting solution was used as a solution for membrane preparation. The above solution was discharged from a ring-shaped part of a tube-in-orifice nozzle while, from a core part thereof, a mixed liquid of 45% by weight of NMP, 45% by weight of TEG and 10% by weight of RO water was discharged as a core liquid and, after passing through an air gap, it was introduced into a coagulation bath which was filled with an outer coagulation liquid consisting of a mixed liquid of 30% by weight of NMP, 30% by weight of TEG and 40% by weight of RO water. At that time, nozzle temperature was set at 45° C. and outer coagulation liquid temperature was set at 30° C. After being pulled out from the coagulation bath, it was made to run in a washing bath of 55° C. to conduct an online washing and, after that, it was wound up using a winding machine.

By subjecting the wound-up hollow fiber membrane to the same treatment as in the step shown in Example 1, the aimed bundle was prepared.

In the resulting hollow fiber membrane, the inner diameter was 205 μm and the membrane thickness was 55 μm. When a micromodule was prepared and the pure water flux was measured, it was found to be 196 L/(m$^2$·h·bar). From the observation of an SEM image and of a cross section after filtration of gold colloid, a dense layer was noted on the outer side only. Further, the amount of a VA copolymer existing in the whole membrane (NMR measurement) and the amount of a VA copolymer existing near the outer surface (IR measurement) were 6.5% by weight and 6.7% by weight, respectively and the ratio of IR/NMR was 1.03. Accordingly, it is likely that the VA copolymer was homogeneously dispersed. The amount of HPC was 2.0% by weight. Since there is no difference, it is likely that the VA copolymer was homogenously dispersed. The breaking strength and burst pressure of the hollow fiber membrane were 45 g/filament and 7.5 bar, respectively. The burst pressure was slightly low. Further, in the constant pressure filtration of IVIG, the recovery rate was 96%. Also, in the constant rate filtration of IVIG, 1005 g/m$^2$ of IVIG could be recovered. As a result of measurement for a virus removing ability using øX-174, the LRV value was 4.8. Further, the maximum value of the UV absorbance (220 to 350 nm) was 0.023. The above results are shown in Table 1.

Example 5

A membrane was prepared under the same conditions as in Example 1, wound up with a winding machine, subjected to a washing treatment in the same bundle shape and under the same condition as in Example 1 and then subjected to the hot-water treatment and the drying under the same conditions as in Example 1 for three times.

The resulting bundle was immersed in a solution containing 27% by weight of 2-propanol, 0.5% by weight of HPC (weight-average molecular weight: 50000) and 72.5% by weight of RO water and subjected to the same treatment as in Example 1 whereby an aimed bundle was prepared.

In the resulting hollow fiber membrane, the inner diameter was 210 µm and the membrane thickness was 60 µm. When a micromodule was prepared and the pure water flux was measured, it was found to be 175 L/(m$^2$·h·bar). From the observation of an SEM image and of a cross section after filtration of gold colloid, a dense layer was noted on the outer side only. Further, the amount of a VA copolymer existing in the whole membrane (NMR measurement) and the amount of a VA copolymer existing near the outer surface (IR measurement) were 6.8% by weight and 6.5% by weight, respectively and the ratio of IR/NMR was 0.96. Accordingly, it is likely that the VA copolymer was homogeneously dispersed. The amount of HPC was 1.5% by weight. The breaking strength and burst pressure of the hollow fiber membrane were 62 g/filament and >9 bar, respectively. Further, in the constant pressure filtration of IVIG, the recovery rate was >98%. Also, in the constant rate filtration of IVIG, 1500 g/m$^2$ of IVIG could be recovered. As a result of measurement for a virus removing ability using øX-174, the LRV value was >5.5. Further, the maximum value of the UV absorbance (220 to 350 nm) was 0.041. The above results are shown in Table 1.

Example 6

A membrane was prepared under the same conditions as in Example 1, wound up with a winding machine, subjected to a washing treatment in the same bundle shape and under the same condition as in Example 1 and then subjected to the hot-water treatment and the drying under the same conditions as in Example 1 for three times.

The resulting bundle was immersed in a solution containing 15% by weight of ethanol manufactured by Nakarai Tesque, 0.1% by weight of HPC (weight-average molecular weight: 140000) and 84.9% by weight of RO water and subjected to the same treatment as in Example 1 whereby an aimed bundle was prepared.

In the resulting hollow fiber membrane, the inner diameter was 195 µm and the membrane thickness was 60 µm. When a micromodule was prepared and the pure water flux was measured, it was found to be 197 L/(m$^2$·h·bar). From the observation of an SEM image and of a cross section after filtration of gold colloid, a dense layer was noted on the outer side only. Further, the amount of a VA copolymer existing in the whole membrane (NMR measurement) and the amount of a VA copolymer existing near the outer surface (IR measurement) were 7.9% by weight and 7.2% by weight, respectively and the ratio of IR/NMR was 0.91. Accordingly, it is likely that the VA copolymer was homogeneously dispersed. The amount of HPC was 0.8% by weight. The breaking strength and burst pressure of the hollow fiber membrane were 65 g/filament and >9 bar, respectively. Further, in the constant pressure filtration of IVIG, the recovery rate was >98%. Also, in the constant rate filtration of IVIG, 2800 g/m$^2$ of IVIG could be recovered. As a result of measurement for a virus removing ability using øX-174, the LRV value was >5.5. Further, the maximum value of the UV absorbance (220 to 350 nm) was 0.042. The above results are shown in Table 1.

Example 7

PES (27% by weight), 7% by weight of VA65/35 (Luvitec (registered trade mark) VA6535), 29.7% by weight of NMP and 36.3% by weight of TEG were mixed and dissolved at 55° C. to give a homogeneous solution. Further, this solution was defoamed under tightly sealing in vacuo and the resulting solution was used as a solution for membrane preparation. The above solution was discharged from a ring-shaped part of a tube-in-orifice nozzle while, from a core part thereof, a mixed liquid of 42.75% by weight of NMP, 52.25% by weight of TEG and 5% by weight of RO water was discharged as a core liquid and, after passing through an air gap, it was introduced into a coagulation bath which was filled with an outer coagulation liquid consisting of a mixed liquid of 27% by weight of NMP, 33% by weight of TEG and 40% by weight of RO water. At that time, nozzle temperature was set at 50° C. and outer coagulation liquid temperature was set at 30° C. After being pulled out from the coagulation bath, it was made to run in a washing bath of 55° C. to conduct an online washing and, after that, it was wound up using a winding machine.

By subjecting the wound-up hollow fiber membrane to the same treatment as in the step shown in Example 1, the aimed bundle was prepared.

In the resulting hollow fiber membrane, the inner diameter was 195 µm and the membrane thickness was 59 µm. When a micromodule was prepared and the pure water flux was measured, it was found to be 190 L/(m$^2$·h·bar). From the observation of an SEM image and of a cross section after filtration of gold colloid, a dense layer was noted on the outer side only. Further, the amount of a VA copolymer existing in the whole membrane (NMR measurement) and the amount of a VA copolymer existing near the outer surface (IR measurement) were 7.5% by weight and 7.6% by weight, respectively and the ratio of IR/NMR was 1.01. Accordingly, it is likely that the VA copolymer was homogeneously dispersed. The amount of HPC was 1.3% by weight. The breaking strength and burst pressure of the hollow fiber membrane were 65 g/filament and >9 bar, respectively. Further, in the constant pressure filtration of IVIG, the recovery rate was >98%. Also, in the constant rate filtration of IVIG, 2030 g/m² of IVIG could be recovered. As a result of measurement for a virus removing ability using øX-174, the LRV value was >5.5. Further, the maximum value of the UV absorbance (220 to 350 nm) was 0.069. The above results are shown in Table 1.

Example 8

A membrane was prepared under the same conditions as in Example 1, wound up with a winding machine, subjected to a washing treatment in the same bundle shape and under the same condition as in Example 1 and then subjected to the hot-water treatment and the drying under the same conditions as in Example 1 for three times.

The resulting bundle was immersed in a solution containing 20% by weight of 2-propanol, 0.1% by weight of curdlan manufactured by Kirin Kyowa Foods Co., Ltd. and 79.9% by weight of RO water, wherein pH of the solution was adjusted to 12, and subjected to the same treatment as in Example 1 whereby an aimed bundle was prepared.

In the resulting hollow fiber membrane, the inner diameter was 195 μm and the membrane thickness was 59 μm. When a micromodule was prepared and the pure water flux was measured, it was found to be 170 L/(m²·h·bar). From the observation of an SEM image and of a cross section after filtration of gold colloid, a dense layer was noted on the outer side only. Further, the amount of a VA copolymer existing in the whole membrane (NMR measurement) and the amount of a VA copolymer existing near the outer surface (IR measurement) were 7.3% by weight and 7.5% by weight, respectively and the ratio of IR/NMR was 1.03. Accordingly, it is likely that the VA copolymer was homogeneously dispersed. The amount of curdlan was 0.7% by weight. The breaking strength and burst pressure of the hollow fiber membrane were 66 g/filament and >9 bar, respectively. Further, in the constant pressure filtration of IVIG, the recovery rate was 96%. Also, in the constant rate filtration of IVIG, 1050 g/m² of IVIG could be recovered. As a result of measurement for a virus removing ability using øX-174, the LRV value was >5.5. Further, the maximum value of the UV absorbance (220 to 350 nm) was 0.048. The above results are shown in Table 1.

Example 9

The same solution for membrane preparation as in Example 1 was prepared. The discharging amount was adjusted so as to make the inner diameter of the hollow fiber membrane 300 μm and the membrane thickness 70 μm. With regard to the steps thereafter, the same treatment as in the steps shown in Example 1 was conducted whereby an aimed bundle was prepared.

In the resulting hollow fiber membrane, the inner diameter was 302 μm and the membrane thickness was 72 μm. When a micromodule was prepared and the pure water flux was measured, it was found to be 157 L/(m²·h·bar). From the observation of an SEM image and of a cross section after filtration of gold colloid, a dense layer was noted on the outer side only. Further, the amount of a VA copolymer existing in the whole membrane (NMR measurement) and the amount of a VA copolymer existing near the outer surface (IR measurement) were 7.9% by weight and 7.8% by weight, respectively and the ratio of IR/NMR was 0.99. Accordingly, it is likely that the VA copolymer was homogeneously dispersed. The amount of HPC was 1.1% by weight. The breaking strength and burst pressure of the hollow fiber membrane were 85 g/filament and >9 bar, respectively. Further, in the constant pressure filtration of IVIG, the recovery rate was 97%. Also, in the constant rate filtration of IVIG, 2008 g/m² of IVIG could be recovered. As a result of measurement for a virus removing ability using øX-174, the LRV value was >5.5. Further, the maximum value of the UV absorbance (220 to 350 nm) was 0.061. The above results are shown in Table 1.

Example 10

PSf (UDEL (registered trade mark) P3500 manufactured by Amoco) (25% by weight), 8% by weight of VA6/4 (Luvitec (registered trade mark) VA 64) manufactured by BASF, 30.15% by weight of NMP manufactured by Mitsubishi Chemical and 36.25% by weight of TEG manufactured by Mitsui Chemical were mixed and dissolved at 50° C. to give a homogeneous solution. Further, this solution was defoamed under tightly sealing in vacuo and the resulting solution was used as a solution for membrane preparation. The above solution was discharged from a ring-shaped part of a tube-in-orifice nozzle while, from a core part thereof, a mixed liquid of 42.75% by weight of NMP, 52.25% by weight of TEG and 5% by weight of RO water was discharged as a core liquid and, after passing through an air gap, it was introduced into a coagulation bath which was filled with an outer coagulation liquid consisting of a mixed liquid of 27% by weight of NMP, 33% by weight of TEG and 40% by weight of RO water. At that time, nozzle temperature was set at 50° C. and outer coagulation liquid temperature was set at 30° C. After being pulled out from the coagulation bath, it was made to run in a washing bath of 55° C. to conduct an online washing and, after that, it was wound up using a winding machine.

The wound-up hollow fiber membranes were made into a bundle of 40 cm length consisting of 5000 membranes. For a purpose of removing the core liquid therefrom, the bundle in a standing state was allowed as it was for 30 minutes. After that, it was immersed in RO water of 85° C. in a straightly standing state to subject to a washing treatment. The liquid in the warm water tank was exchanged for five times so as to repeat the washing treatment. After that, the bundle being still in a wet state was quickly immersed in warm water of 40° C. placed in a high-pressure steam sterilizing machine and subjected to a treatment with hot water at high pressure under the condition of 140° C. for 20 minutes. After that, it was dried by means of microwave with the temperature in the device of 35° C. The high-pressure steam treatment and drying were repeated for three times.

The resulting bundle was immersed in a solution containing 20% by weight of 2-propanol manufactured by Nakarai Tesque, 0.5% by weight of HPC (weight-average molecular weight: 50000) manufactured by Nippon Soda and 79.5% by weight of RO water at 25° C., the container was tightly closed and then quickly depressurized down to −0.07 MPa. After being allowed to stand for 20 minutes, the container was returned to ordinary pressure, and then the bundle was taken out therefrom. The bundle was allowed to stand for 5 minutes in a standing state in order to remove the treating liquid therefrom. After that, it was immersed in RO water of 80° C. in a straightly standing state and a gelling treatment was conducted for 1 hour. After that, drying by means of microwave was conducted with the temperature in the device of 35° C. whereby a bundle was prepared.

In the resulting hollow fiber membrane, the inner diameter was 195 μm and the membrane thickness was 60 μm.

When a micromodule was prepared and the pure water flux was measured, it was found to be 145 L/(m²·h·bar). From the observation of an SEM image and of a cross section after filtration of gold colloid, a dense layer was noted on the outer side only. Further, the amount of a VA copolymer existing in the whole membrane (NMR measurement) and the amount of a VA copolymer existing near the outer surface (IR measurement) were 7.2% by weight and 7.0% by weight, respectively and the ratio of IR/NMR was 0.97. Accordingly, it is likely that the VA copolymer was homogeneously dispersed. The amount of HPC was 1.5% by weight. The breaking strength and burst pressure of the hollow fiber membrane were 42 g/filament and >9 bar, respectively. Further, in the constant pressure filtration of IVIG, the recovery rate was >98%. Also, in the constant rate filtration of IVIG, 975 g/m² of IVIG could be recovered. As a result of measurement for a virus removing ability using ⌀X-174, the LRV value was >5.5. Further, the maximum value of the UV absorbance (220 to 350 nm) was 0.035. The above results are shown in Table 1.

Comparative Example 1

A membrane was prepared under the same conditions as in Example 1, wound up with a winding machine, subjected to a washing treatment in the same bundle shape and under the same condition as in Example 1 and then subjected to the hot-water treatment and the drying under the same conditions as in Example 1 for three times. The resulting bundle was not subjected to the treatment for adhering the second hydrophilic polymer to the surface of the hollow fiber membrane.

In the resulting hollow fiber membrane, the inner diameter was 196 μm and the membrane thickness was 60 μm. When a micromodule was prepared and the pure water flux was measured, it was found to be 185 L/(m²·h·bar). From the observation of an SEM image and of a cross section after filtration of gold colloid, a dense layer was noted on the outer side only. Further, the amount of a VA copolymer existing in the whole membrane (NMR measurement) and the amount of a VA copolymer existing near the outer surface (IR measurement) were 9.8% by weight and 10.4% by weight, respectively and the ratio of IR/NMR was 1.06. Accordingly, it is likely that the VA copolymer was homogeneously dispersed. The amount of HPC was 0.0% by weight. The breaking strength and burst pressure of the hollow fiber membrane were 67 g/filament and >9 bar, respectively. Further, in the constant pressure filtration of IVIG, the recovery rate was >98%. Also, in the constant rate filtration of IVIG, 950 g/m² of IVIG could be recovered. As a result of measurement for a virus removing ability using ⌀X-174, the LRV value was >5.5. However, the maximum value of the UV absorbance (220 to 350 nm) was 0.210. Since an excessive VA6/4 was not removed, the UV absorbance became high. The above results are shown in Table 2.

Comparative Example 2

A membrane was prepared under the same conditions as in Example 1, wound up with a winding machine, subjected to a washing treatment in the same bundle shape and under the same condition as in Example 1 and then subjected to the hot-water treatment and the drying under the same conditions as in Example 1 for three times.

A solution containing 20% by weight of 2-propanol and 80% by weight of RO water into which no hydrophilizing agent was dissolved was prepared. The resulting bundle was subjected to the same treatment as in Example 1 using the prepared solution to give an aimed bundle.

In the resulting hollow fiber membrane, the inner diameter was 195 μm and the membrane thickness was 57 μm. When a micromodule was prepared and the pure water flux was measured, it was found to be 190 L/(m²·h·bar). From the observation of an SEM image and of a cross section after filtration of gold colloid, a dense layer was noted on the outer side only. Further, the amount of a VA copolymer existing in the whole membrane (NMR measurement) and the amount of a VA copolymer existing near the outer surface (IR measurement) were 7.3% by weight and 7.5% by weight, respectively and the ratio of IR/NMR was 1.03. Accordingly, it is likely that the VA copolymer was homogeneously dispersed. The amount of HPC was 0.0% by weight. The breaking strength and burst pressure of the hollow fiber membrane were 68 g/filament and >9 bar, respectively. Further, in the constant pressure filtration of IVIG, the recovery rate was 93%, which indicated decrease of the treating amount. Also, in the constant rate filtration of IVIG, 300 g/m² of IVIG could be recovered. As a result of measurement for a virus removing ability using ⌀X-174, the LRV value was >5.5. The maximum value of the UV absorbance (220 to 350 nm) was 0.031. With regard to the reason why the treating amount of the IVIG decreased, it is likely that, although an excessive VA6/4 was removed by an aqueous solution of ethanol, there was no hydrophilization by the second hydrophilic polymer and inhibition of adsorption of protein was insufficient whereby it is likely that the treating amount for a protein solution became low. The above results are shown in Table 2.

Comparative Example 3

PES (20% by weight), 6% by weight of PVP (polyvinylpyrrolidone Luvitec (registered trade mark) K85) manufactured by BASF, 33.3% by weight of NMP and 40.7% by weight of TEG were mixed and dissolved at 55° C. to give a homogeneous solution. Further, this solution was defoamed under tightly sealing in vacuo and the resulting solution was used as a solution for membrane preparation. The above solution was discharged from a ring-shaped part of a tube-in-orifice nozzle while, from a core part thereof, a mixed liquid of 40.5% by weight of NMP, 49.5% by weight of TEG and 10% by weight of RO water was discharged as a core liquid and, after passing through an air gap, it was introduced into a coagulation bath which was filled with an outer coagulation liquid consisting of a mixed liquid of 27% by weight of NMP, 33% by weight of TEG and 40% by weight of RO water. At that time, nozzle temperature was set at 55° C. and outer coagulation liquid temperature was set at 60° C. After being pulled out from the coagulation bath, it was made to run in a washing bath of 55° C. to conduct an online washing and, after that, it was wound up using a winding machine.

By subjecting the wound-up hollow fiber membrane to the same treatment as in the step shown in Example 1, the aimed bundle was prepared.

In the resulting hollow fiber membrane, the inner diameter was 192 μm and the membrane thickness was 63 μm. When a micromodule was prepared and the pure water flux was measured, it was found to be 136 L/(m²·h·bar). From the observation of an SEM image and of a cross section after filtration of gold colloid, a dense layer was noted on both of the inner side and outer side of the hollow fiber membrane. Further, the amount of PVP existing in the whole membrane (NMR measurement) and the amount of PVP existing near the outer surface (IR measurement) were 3.5% by weight and 7.6% by weight, respectively and the ratio of IR/NMR was 2.17. Accordingly, it is likely that PVP was not homogeneously dispersed but was abundantly distributed near the outer surface. The amount of HPC contained therein was 1.3% by weight. The reason why the membrane structure is in such a one that a dense layer is formed on both of the inner and outer surfaces and the distribution of PVP is not homogeneous is presumed to be caused by the difference between the interaction of PES and PVP and the interaction of PES and VA6/4. When the spinning dope is coagulated to form a membrane, VA6/4 and PVP are gelled immediately in a state of being incorporated into PES near the inner and outer surfaces acting as the starting point for the coagulation whereby a dense structure is apt to be formed. The control is conducted mostly by the concentration of the coagulation liquid (concentration of core liquid in the inner surface while, in the outer surface, concentration of coagulation liquid). With this regard, tendency for the coagulation is stronger in a combination of PES with PVP and a dense layer is apt to be formed even at high concentration whereby a dense structure is formed even in the inner surface. In addition, in a relatively sparse part of a middle area of the membrane which is coagulated gradually and which occupies most of the membrane, VA6/4 is stably coagulated in a compatible state during a process wherein PES is compatible with VA6/4 or PVP followed by coagulating but, since an abundant amount of PVP is dropped out to a liquid phase and washed out, its total amount contained therein decreases. Due to the changes in the membrane structure and the composition as such, the recovery rate decreased to 92% in a constant pressure filtration of the IVIG solution and, in a constant rate filtration of the IVIG solution, the recovery rate became 123 g/m$^2$ showing low efficiencies. The breaking strength and burst pressure of the hollow fiber membrane were 35 g/filament and 7.8 bar, respectively. As a result of measurement for a virus removing ability using øX-174, the LRV value was >5.5. Further, the maximum value of the UV absorbance (220 to 350 nm) was 0.021. The above results are shown in Table 2.

Comparative Example 4

PES (27% by weight), 9% by weight of VA6/4, 28.8% by weight of NMP and 35.2% by weight of TEG were mixed and dissolved at 55° C. to give a homogeneous solution. Further, this solution was defoamed under tightly sealing in vacuo and the resulting solution was used as a solution for membrane preparation. The above solution was discharged from a ring-shaped part of a tube-in-orifice nozzle while, from a core part thereof, a mixed liquid of 27% by weight of NMP, 33% by weight of TEG and 40% by weight of RO water was discharged as a core liquid and, after passing through an air gap, it was introduced into a coagulation bath which was filled with an outer coagulation liquid consisting of a mixed liquid of 38.25% by weight of NMP, 46.75% by weight of TEG and 15% by weight of RO water. At that time, nozzle temperature was set at 50° C. and outer coagulation liquid temperature was set at 60° C. After being pulled out from the coagulation bath, it was made to run in a washing bath of 55° C. to conduct an online washing and, after that, it was wound up using a winding machine.

By subjecting the wound-up hollow fiber membrane to the same treatment as in the step shown in Example 1, the aimed bundle was prepared.

In the resulting hollow fiber membrane, the inner diameter was 195 µm and the membrane thickness was 60 µm. When a micromodule was prepared and the pure water flux was measured, it was found to be 310 L/(m$^2$·h·bar). From the observation of an SEM image and of a cross section after filtration of gold colloid, a dense layer was noted on the inner surface only. The amount of a VA copolymer existing in the whole membrane (NMR measurement) and the amount of a VA copolymer existing near the outer surface (IR measurement) were 7.1% by weight and 4.2% by weight, respectively and the ratio of IR/NMR was 0.59. Accordingly, the distribution of VA6/4 near the outer surface is small and it is likely that the VA copolymer is not homogeneously dispersed. The amount of HPC contained therein was 1.1% by weight. With regard to the reason why a dense layer was formed on the inner surface and the amount of VA/64 in the outer surface decreased, its details are ambiguous but it is likely that, since a dense layer was formed on the inner surface due to a low core liquid concentration and a dense layer formation on the outer surface was suppressed due to high concentration of a coagulation liquid, densification of the layer took place only on the inner surface and the amount of a washing solution passing through the outer surface having a big pore size increased and that, as a result thereof, the amount of VA6/4 contained therein decreased. The breaking strength and burst pressure of the hollow fiber membrane were 65 g/filament and >9 bar, respectively. Further, in the constant pressure filtration of IVIG, the recovery rate was 93%, which indicated low recovery rate. Also, in the constant rate filtration of IVIG, 50 g/m$^2$ of IVIG could be recovered. As a result of measurement for a virus removing ability using øX-174, the LRV value was >5.5. Further, the maximum value of the UV absorbance (220 to 350 nm) was 0.065. The reason why the treating amount of protein decreased was likely to be due to the fact that, during the filtration, protein causes a clogging in the dense layer on the inner surface side and, as a result, the treating amount quickly decreased. The above results are shown in Table 2.

Comparative Example 5

Spinning was carried out under the conditions of Comparative Example 3 and winding-up was done using a winding machine. After that, washing and drying were conducted under the conditions as shown in Example 1 to prepare a bundle.

The resulting bundle was immersed in a solution containing 20% by weight of 2-propanol, 0.5% by weight of VA6/4 and 79.5% by weight of RO water at 25° C., the container was tightly closed and then quickly depressurized down to −0.07 MPa. After being allowed to stand for 20 minutes, the container was returned to ordinary pressure, and then the bundle was taken out therefrom. The bundle was allowed to stand for 5 minutes in a standing state in order to remove the aqueous solution therefrom. After that, drying by means of microwave was conducted with the temperature in the device of 35° C. to give the aimed hollow fiber membrane.

When the pure water flux of the resulting hollow fiber membrane was measured, it was found to be 135 L/(m$^2$·h·bar). From the observation of an SEM image and of a cross section after filtration of gold colloid, a dense layer was noted on both of the inner side and outer side of the hollow fiber membrane. Further, the amount of PVP existing in the whole membrane (NMR measurement) and the amount of PVP existing near the outer surface (IR measurement) were 3.5% by weight and 7.6% by weight, respectively and the ratio of IR/NMR was 2.17. Accordingly, it is likely that PVP was not homogeneously dispersed but was abundantly distributed near the outer surface. The breaking strength and burst pressure of the hollow fiber membrane were 35 g/filament and 7.8 bar, respectively. Further, in the constant pressure filtration of IVIG, the recovery rate was 91%. Also, in the constant rate filtration of IVIG, 110 g/m² of IVIG could be recovered. As a result of measurement for a virus removing ability using øX-174, the LRV value was >5.5. Further, the maximum value of the UV absorbance (220 to 350 nm) was 0.045. In the case of immersion into the VA6/4 solution, it was likely that the VA6/4 was not coated on the surface of the membrane or was immediately dropped out and accordingly that no sufficient hydrophilization was achieved. The above results are shown in Table 2.

Comparative Example 6

PES (27% by weight), 32.85% by weight of NMP and 40.15% by weight of TEG were mixed and dissolved at 55° C. to give a homogeneous solution. Further, this solution was defoamed under tightly sealing in vacuo and the resulting solution was used as a solution for membrane preparation. The above solution was discharged from a ring-shaped part of a tube-in-orifice nozzle while, from a core part thereof, a mixed liquid of 13.5% by weight of NMP, 16.5% by weight of TEG and 70% by weight of RO water was discharged as a core liquid and, after passing through an air gap, it was introduced into a coagulation bath which was filled with an outer coagulation liquid consisting of a mixed liquid of 2.25% by weight of NMP, 2.75% by weight of TEG and 95% by weight of RO water. At that time, nozzle temperature was set at 50° C. and outer coagulation liquid temperature was set at 60° C. After being pulled out from the coagulation bath, it was made to run in a washing bath of 55° C. to conduct an online washing and, after that, it was wound up using a winding machine.

By subjecting the wound-up hollow fiber membrane to the same treatment as in the step shown in Example 1, the aimed bundle was prepared.

In the resulting hollow fiber membrane, the inner diameter was 200 µm and the membrane thickness was 56 µm. When a micromodule was prepared and the pure water flux was measured, it was found to be 815 L/(m²·h·bar). From the observation of an SEM image and of a cross section after filtration of gold colloid, a dense layer was noted on the inner side only. The amount of HPC was 1.2% by weight. The breaking strength and burst pressure of the hollow fiber membrane were 55 g/filament and >9 bar, respectively. In a constant pressure filtration of IVIG, clogging happened whereby the expected filtration was not possible. Moreover, in a constant rate filtration of IVIG, clogging also happened immediately whereby no filtration was possible. When øX-174 was measured as a virus removing ability, the LRV value was 4.5. Since a membrane was prepared without the use of VA6/4, control of the membrane structure was not possible whereby the pore size through which IVIG can be filtrated could not be maintained. The above results are shown in Table 2.

Comparative Example 7

A membrane was spinned under the same conditions as in Comparative Example 6, wound-up with a winding machine, subjected to a washing treatment in the same bundle shape and under the same condition as in Example 1 and then subjected to the hot-water treatment and the drying under the same conditions as in Example 1 for three times.

The resulting bundle was immersed in a solution containing 20% by weight of 2-propanol, 0.5% by weight of VA6/4 and 79.5% by weight of RO water at 25° C., the container was tightly closed and then quickly depressurized down to −0.07 MPa. After being allowed to stand for 20 minutes, the container was returned to ordinary pressure, and then the bundle was taken out therefrom. The bundle was allowed to stand for 5 minutes in a standing state in order to remove the treatment solution therefrom. After that, drying by means of microwave was conducted with the temperature in the device of 35° C.

The resulting bundle was immersed in a solution containing 20% by weight of 2-propanol, 0.5% by weight of HPC (weight-average molecular weight: 50000) and 79.5% by weight of RO water at 25° C., the container was tightly closed and then quickly depressurized down to −0.07 MPa. After being allowed to stand for 20 minutes, the container was returned to ordinary pressure, and then the bundle was taken out therefrom. The bundle was allowed to stand for 5 minutes in a standing state in order to remove the treatment solution therefrom. After that, it was immersed in RO water of 80° C. in a straightly standing state and a gelling treatment was conducted for 1 hour. After that, drying by means of microwave was conducted with the temperature in the device of 35° C. to give the aimed hollow fiber membrane.

In the resulting hollow fiber membrane, the inner diameter was 199 µm and the membrane thickness was 57 µm. When a micromodule was prepared and the pure water flux was measured, it was found to be 720 L/(m²·h·bar). From the observation of an SEM image, a dense layer was noted on the inner side. According to the measurement by NMR, no VA6/4 was detected and no coat was formed. Amount of the HPC contained therein was 1.2% by weight. Breaking strength and burst pressure of the hollow fiber membrane were 55 g/filament and >9 bar, respectively. In a constant pressure filtration of IVIG, clogging happened whereby the expected filtration was not possible. Moreover, in a constant rate filtration of IVIG, clogging also happened immediately whereby no filtration was possible. When øX-174 was measured as a virus removing ability, the LRV value was 4.5. In the preparation of membrane using a spinning dope to which no VA6/4 was added, control of the structure was difficult and coating of VA6/4 was impossible. Accordingly, even when a coating was conducted using HPC to a membrane having small pore size, the result was that no protein could be permeated. The above results are shown in Table 2.

TABLE 1

|  | Example 1 | Example 2 | Example 3 | Example 4 | Example 5 |
| --- | --- | --- | --- | --- | --- |
| Inner diameter (µm) | 195 | 185 | 200 | 205 | 210 |
| Membrane thickness (µm) | 59 | 55 | 59 | 55 | 60 |
| Pure water flux (L/(m² · h · bar)) | 190 | 170 | 135 | 196 | 175 |
| Structure | only the outer layer has a dense layer | only the outer layer has a dense layer | only the outer layer has a dense layer | only the outer layer has a dense layer | only the outer layer has a dense layer |

TABLE 1-continued

|  | | | | | |
|---|---|---|---|---|---|
| Kinds of hydrophobic polymer | PES | PES | PES | PES | PES |
| Kinds of first hydrophilic polymer | VA copolymer (VA6/4) | VA copolymer (VA6/4) | VA copolymer (VA6/4) | VA copolymer (VA6/4) | VA copolymer (VA6/4) |
| Kinds of second hydrophilic polymer | HPC | HPC | HPC | HPC | HPC |
| First hydrophilic polymer NMR(%) | 7.6 | 7.1 | 7.6 | 6.5 | 6.8 |
| First hydrophilic polymer IR(%) | 7.1 | 7 | 7.6 | 6.7 | 6.5 |
| IR/NMR | 0.93 | 0.99 | 1 | 1.03 | 0.96 |
| Second hydrophilic polymer NMR(%) | 1.3 | 1.2 | 1.7 | 2 | 1.5 |
| Breaking strength (g/filament) | 67 | 78 | 52 | 45 | 62 |
| Burst strength (burst pressure) (bar) | >9 | >9 | >9 | 7.5 | >9 |
| Removing rate for φX-174 (LRV value) | >5.5 | >5.5 | >5.5 | 4.8 | >5.5 |
| Recovery rate of 1% IVIG in constant pressure filtration (%) | >98 | >98 | 97 | 96 | >98 |
| Recovery rate of 1% IVIG in constant rate filtration (g/m$^2$) | 2750 | 950 | 876 | 1005 | 1500 |
| UV absorbance (220-350 nm) | 0.051 | 0.036 | 0.062 | 0.023 | 0.041 |

|  | Example 6 | Example 7 | Example 8 | Example 9 | Example 10 |
|---|---|---|---|---|---|
| Inner diameter (μm) | 195 | 195 | 195 | 302 | 195 |
| Membrane thickness (μm) | 60 | 59 | 59 | 72 | 60 |
| Pure water flux (L/(m$^2$ · h · bar)) | 197 | 190 | 170 | 157 | 145 |
| Structure | only the outer layer has a dense layer | only the outer layer has a dense layer | only the outer layer has a dense layer | only the outer layer has a dense layer | only the outer layer has a dense layer |
| Kinds of hydrophobic polymer | PES | PES | PES | PES | PSf |
| Kinds of first hydrophilic polymer | VA copolymer (VA6/4) | VA copolymer (VA65/35) | VA copolymer (VA6/4) | VA copolymer (VA6/4) | VA copolymer (VA6/4) |
| Kinds of second hydrophilic polymer | HPC | HPC | curdlan | HPC | HPC |
| First hydrophilic polymer NMR(%) | 7.9 | 7.5 | 7.3 | 7.9 | 7.2 |
| First hydrophilic polymer IR(%) | 7.2 | 7.6 | 7.5 | 7.8 | 7.0 |
| IR/NMR | 0.91 | 1.01 | 1.03 | 0.99 | 0.97 |
| Second hydrophilic polymer NMR(%) | 0.8 | 1.3 | 0.7 | 1.1 | 1.5 |
| Breaking strength (g/filament) | 65 | 65 | 66 | 85 | 42 |
| Burst strength (burst pressure) (bar) | >9 | >9 | >9 | >9 | >9 |
| Removing rate for φX-174 (LRV value) | >5.5 | >5.5 | >5.5 | >5.5 | >5.5 |
| Recovery rate of 1% IVIG in constant pressure filtration (%) | >98 | >98 | 96 | 97 | >98 |
| Recovery rate of 1% IVIG in constant rate filtration (g/m$^2$) | 2800 | 2030 | 1050 | 2008 | 975 |
| UV absorbance (220-350 nm) | 0.042 | 0.069 | 0.048 | 0.061 | 0.035 |

TABLE 2

|  | Comparative Example 1 | Comparative Example 2 | Comparative Example 3 | Comparative Example 4 |
|---|---|---|---|---|
| Inner diameter (μm) | 196 | 195 | 192 | 195 |
| Membrane thickness (μm) | 60 | 57 | 63 | 60 |
| Pure water flux (L/(m$^2$ · h · bar)) | 185 | 190 | 136 | 310 |
| Structure | only the outer layer has a dense layer | only the outer layer has a dense layer | the outer layer and the inner layer have a dense layer | only the inner layer has a dense layer |
| Kinds of hydrophobic polymer | PES | PES | PES | PES |
| Kinds of first hydrophilic polymer | VA copolymer (VA6/4) | VA copolymer (VA6/4) | PVP | VA copolymer (VA6/4) |
| Kinds of second hydrophilic polymer | — | — | HPC | HPC |
| First hydrophilic polymer NMR(%) | 9.8 | 7.3 | 3.5 | 7.1 |
| First hydrophilic polymer IR(%) | 10.4 | 7.5 | 7.6 | 4.2 |
| IR/NMR | 1.06 | 1.03 | 2.17 | 0.59 |
| Second hydrophilic polymer NMR(%) | 0 | 0 | 1.3 | 1.1 |
| Breaking strength (g/filament) | 67 | 68 | 35 | 65 |
| Burst strength (burst pressure) (bar) | >9 | >9 | 7.8 | >9 |
| Removing rate for φX-174 (LRV value) | >5.5 | >5.5 | >5.5 | >5.5 |
| Recovery rate of 1% IVIG in constant pressure filtration (%) | >98 | 93 | 92 | 93 |
| Recovery rate of 1% IVIG in constant rate filtration (g/m$^2$) | 950 | 300 | 123 | 50 |
| UV absorbance (220-350 nm) | 0.21 | 0.031 | 0.021 | 0.065 |

TABLE 2-continued

|  | Comparative Example 5 | Comparative Example 6 | Comparative Example 7 |
|---|---|---|---|
| Inner diameter (μm) | 192 | 200 | 199 |
| Membrane thickness (μm) | 63 | 56 | 57 |
| Pure water flux (L/(m² · h · bar)) | 135 | 815 | 720 |
| Structure | the outer layer and the inner layer have a dense layer | only the inner layer has a dense layer | only the inner layer has a dense layer |
| Kinds of hydrophobic polymer | PES | PES | PES |
| Kinds of first hydrophilic polymer | PVP | — | — |
| Kinds of second hydrophilic polymer | VA copolymer (VA6/4) | HPC | VA copolymer (VA6/4) |
| First hydrophilic polymer NMR(%) | 3.5 | — | — |
| First hydrophilic polymer IR(%) | 7.6 | — | — |
| IR/NMR | 2.17 | — | — |
| Second hydrophilic polymer NMR(%) | — | 1.2 | 1.2 |
| Breaking strength (g/filament) | 35 | 55 | 55 |
| Burst strength (burst pressure) (bar) | 7.8 | >9 | >9 |
| Removing rate for φX-174 (LRV value) | >5.5 | 4.5 | 4.5 |
| Recovery rate of 1% IVIG in constant pressure filtration (%) | 91 | — | — |
| Recovery rate of 1% IVIG in constant rate filtration (g/m²) | 110 | — | — |
| UV absorbance (220-350 nm) | 0.045 | — | — |

INDUSTRIAL APPLICABILITY

In the porous hollow fiber membrane in accordance with the present invention, recovery of a permeating substance such as protein and trapping of fine particles such as virus can be efficiently carried out in case a solution containing protein or the like is separated and purified. Accordingly, it can be advantageously used for constructing a separation process with ensured productivity and safety and is expected to greatly contribute in industry.

The invention claimed is:

1. A porous hollow fiber membrane for treatment of a protein-containing liquid, the porous hollow fiber membrane comprising a porous hollow fiber substrate membrane coated with a second hydrophilic polymer,
    wherein the porous hollow fiber substrate membrane comprises a hydrophobic polymer and a first hydrophilic polymer,
    wherein an amount of said first hydrophilic polymer contained in the porous hollow fiber membrane is 5 to 9% by weight,
    wherein a membrane surface of said porous hollow fiber substrate membrane and a pore surface of said porous hollow fiber substrate membrane are coated with the second hydrophilic polymer,
    said hydrophobic polymer is a polysulfone-type polymer,
    said first hydrophilic polymer is a copolymer of vinylpyrrolidone with vinyl acetate and the vinylpyrrolidone and the vinyl acetate have a ratio by weight of 6:4 to 65:35 in said copolymer,
    wherein the polysulfone-type polymer is entangled with the vinyl acetate of the first hydrophilic polymer in the porous hollow fiber substrate membrane;
    said second hydrophilic polymer is a polysaccharide or a polysaccharide derivative,
    wherein the polysaccharide or the polysaccharide derivative is fixed to the vinylpyrrolidone of the first hydrophilic polymer;
    wherein the porous hollow fiber membrane is an asymmetric structure having a dense layer in an outer layer only,
    wherein the protein-containing liquid is filtrated from an inside to an outside of said porous hollow fiber membrane, and
    wherein a ratio by weight (IR/NMR) of an amount (IR) of the first hydrophilic polymer existing near an outer surface by an IR measurement to an amount (NMR) of the first hydrophilic polymer existing in the whole porous hollow fiber membrane by an NMR measurement is 0.9 to 1.1.

2. The porous hollow fiber membrane according to claim 1, wherein said second hydrophilic polymer is a cellulose type polymer.

3. The porous hollow fiber membrane according to claim 1, wherein an amount of said second hydrophilic polymer contained in the porous hollow fiber membrane is 0.5 to 2.5% by weight.

4. The porous hollow fiber membrane according to claim 1,
    wherein an extract prepared from the porous hollow fiber membrane has a maximum absorbance of 0.1 or less when measured under the condition of 200 to 350 nm wavelength range and 1 cm cell length,
    wherein the extract is prepared by such a manner that a 1 g bundle of the porous hollow fiber membrane in a dry state is weighed, immersed in 100 g of water and subjected to an autoclave extraction for 20 minutes with a reaching/retaining temperature of 132° C.

5. A method for manufacturing the porous hollow fiber membrane for the treatment of a protein-containing liquid as claimed in claim 1, comprising forming the porous hollow fiber membrane using a dope prepared by co-dissolving the hydrophobic polymer and the first hydrophilic polymer in the same solvent and then coating the second hydrophilic polymer on the membrane surface and the pore surface of the porous hollow fiber membrane.

6. The porous hollow fiber membrane according to claim 1, wherein the porous hollow fiber membrane has an inner diameter of 150 μm to 310 μm.

7. The porous hollow fiber membrane according to claim 1, wherein the porous hollow fiber membrane has a membrane thickness of 50 μm to 80 μm.

* * * * *